United States Patent
Oishi et al.

(10) Patent No.: US 11,077,033 B2
(45) Date of Patent: Aug. 3, 2021

(54) COMPLEXES OF HYDROTALCITES AND FIBERS

(71) Applicant: NIPPON PAPER INDUSTRIES CO., LTD., Tokyo (JP)

(72) Inventors: Masatoshi Oishi, Tokyo (JP); Naoyuki Sugawara, Tokyo (JP); Shisei Goto, Tokyo (JP)

(73) Assignee: NIPPON PAPER INDUSTRIES CO., LTD., Tokyo (JP)

( * ) Notice: Subject to any disclaimer, the term of this patent is extended or adjusted under 35 U.S.C. 154(b) by 0 days.

(21) Appl. No.: 16/318,368

(22) PCT Filed: Aug. 10, 2017

(86) PCT No.: PCT/JP2017/029131
§ 371 (c)(1),
(2) Date: Jan. 17, 2019

(87) PCT Pub. No.: WO2018/030521
PCT Pub. Date: Feb. 15, 2018

(65) Prior Publication Data
US 2019/0282472 A1 Sep. 19, 2019

(30) Foreign Application Priority Data

Aug. 10, 2016 (JP) .............................. JP2016-158029
Jan. 12, 2017 (JP) .............................. JP2017-003514

(51) Int. Cl.
| | |
|---|---|
| *A61K 9/14* | (2006.01) |
| *A61K 8/26* | (2006.01) |
| *A01N 59/06* | (2006.01) |
| *A61Q 15/00* | (2006.01) |
| *C01F 7/00* | (2006.01) |
| *D06M 11/44* | (2006.01) |
| *D06M 11/45* | (2006.01) |
| *D21H 11/00* | (2006.01) |
| *D21H 17/70* | (2006.01) |
| *D21H 21/36* | (2006.01) |
| *D21H 13/00* | (2006.01) |

(52) U.S. Cl.
CPC .............. *A61K 8/26* (2013.01); *A01N 59/06* (2013.01); *A61Q 15/00* (2013.01); *C01F 7/00* (2013.01); *C01F 7/005* (2013.01); *D06M 11/44* (2013.01); *D06M 11/45* (2013.01); *D21H 11/00* (2013.01); *D21H 13/00* (2013.01); *D21H 17/70* (2013.01); *D21H 21/36* (2013.01); *C01P 2002/22* (2013.01); *C01P 2002/72* (2013.01); *C01P 2004/03* (2013.01); *C01P 2006/10* (2013.01)

(58) Field of Classification Search
CPC . A61K 9/14; A61K 9/13; A61K 9/146; A61K 9/1686; D21H 17/68; D21H 19/00
See application file for complete search history.

(56) References Cited

U.S. PATENT DOCUMENTS

| | | | |
|---|---|---|---|
| 6,180,764 B1 * | 1/2001 | Noweck .................... | C01G 1/00 534/15 |
| 6,376,057 B1 * | 4/2002 | Akao ...................... | B32B 27/10 428/215 |
| 2009/0162658 A1 | 6/2009 | Wolk et al. | |
| 2013/0126116 A1 | 5/2013 | Solismaa | |

FOREIGN PATENT DOCUMENTS

| | | |
|---|---|---|
| EP | 1749131 A1 | 2/2007 |
| JP | H04-263615 A | 9/1992 |
| JP | H07-279089 A | 10/1995 |
| JP | 9-95900 | 4/1997 |
| JP | H09-175819 A | 7/1997 |
| JP | H09-294485 A | 11/1997 |
| JP | H10-226997 A | 8/1998 |
| JP | 2000144522 A * | 5/2000 |
| JP | 2004-360144 A | 12/2004 |
| JP | 2006-206660 A | 8/2006 |
| JP | 2007-262635 A | 10/2007 |
| JP | 2009-143798 A | 7/2009 |
| JP | 2012-144829 A | 8/2012 |
| JP | 2013-085568 A | 5/2013 |
| JP | 2013-536329 A | 9/2013 |
| JP | 2015-193000 A | 11/2015 |
| WO | 2005/111306 A1 | 11/2005 |
| WO | WO-2005111306 A1 * | 11/2005 ............. D21H 17/68 |

OTHER PUBLICATIONS

Mekdad et al (Effect of Mg/Al ratio and of the rate of reinforcement on the synthesis of a nanocomposite Cellulose/Hydrotalcite, Journal of Advances in Chemistry, 2014) (Year: 2014).*
International Search Report for Application No. PCT/JP2017/029131, dated Nov. 14, 2017, 2 pages.
Extended European Search Report for EP Application No. 17839585.1, dated Mar. 27, 2020, 7 pages.
Honda et al., Synthesis and Ion Exchange Properties of Magnesium-Iron (III) and -Aluminum hydrotalcite like compounds. J Ion Exchange. 2005;16(1):41-48.
Kameda et al., Application of hydrotalcite for water environmental preservation and purification. The Chemical Times. 2005;1(195):10-16.
Oshima et al., Ability to Remove Phosphorus from Wastewater Using Hydrotalcite-Carrying Fiber (HTCF). Journal of Japan Society on Water Environment. 2007;30(11):671-676.

(Continued)

*Primary Examiner* — Micah Paul Young
(74) *Attorney, Agent, or Firm* — McCarter & English, LLP; Steven G. Davis; Wei Song

(57) ABSTRACT

The present invention aims to provide techniques for preparing complexes of a hydrotalcite and a fiber. The complexes of a hydrotalcite and a fiber can be synthesized efficiently by synthesizing the hydrotalcite in an aqueous system in the presence of the fiber.

8 Claims, 16 Drawing Sheets

(56) References Cited

OTHER PUBLICATIONS

Seida, Adsorption Behavior of Layered Double Hydroxide for Surfactants during Reconstruction Process from Its Heat-treated Solid Solution and Structural Stability of Its Emulsion Gel. Bulletin of Toyo University, Natural Sciences. 2012;56:43-52.

\* cited by examiner

Fig. 4-1
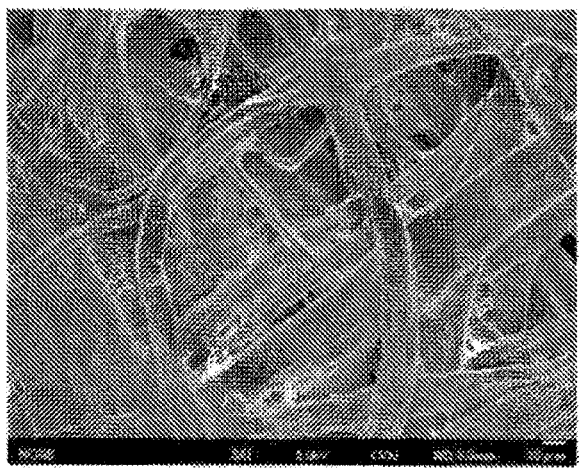
(a) 500X magnification
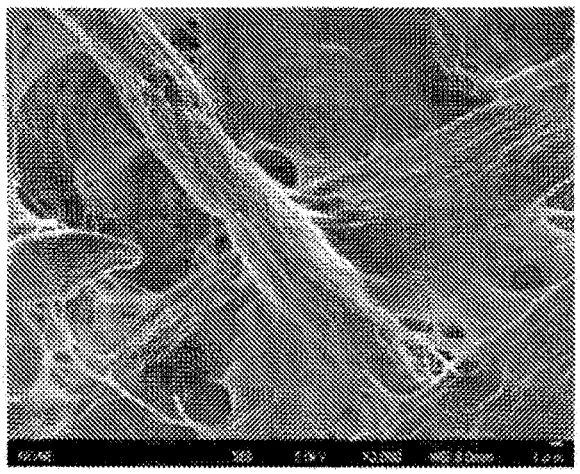
(b) 3000X magnification
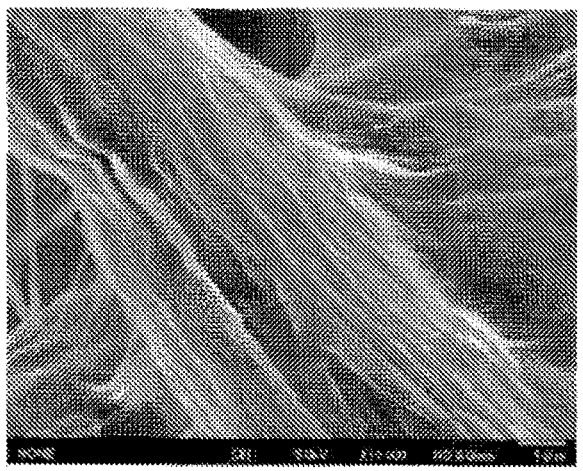
(c) 10000X magnification
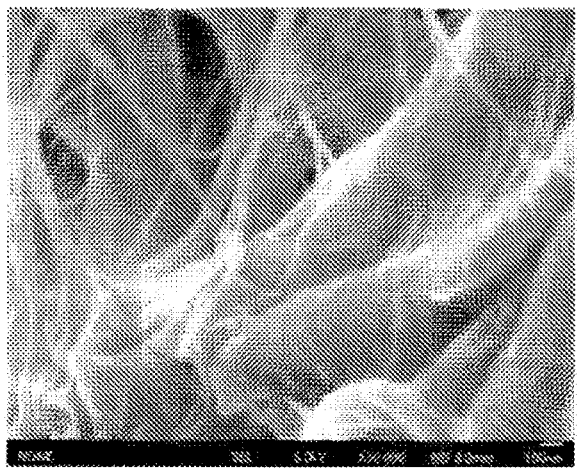
(d) 50000X magnification Fig. 4-2
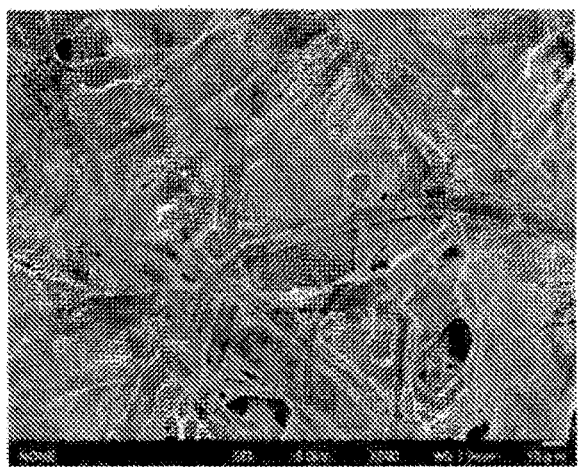
(a) 500X magnification
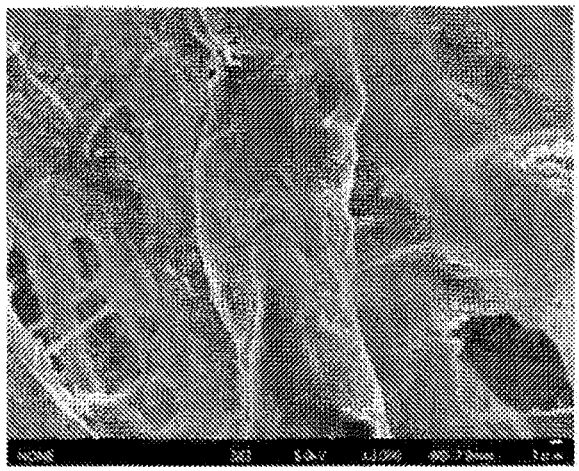
(b) 3000X magnification
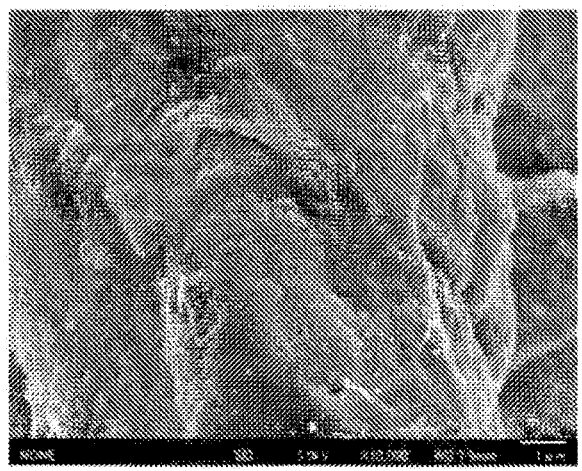
(c) 10000X magnification
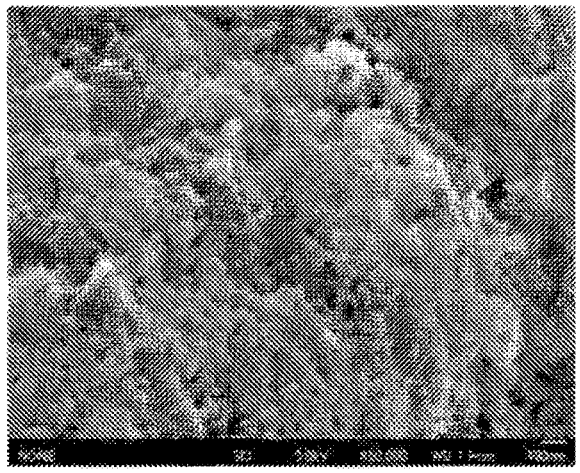
(d) 50000X magnification Fig. 4-3
(a) 500X magnification
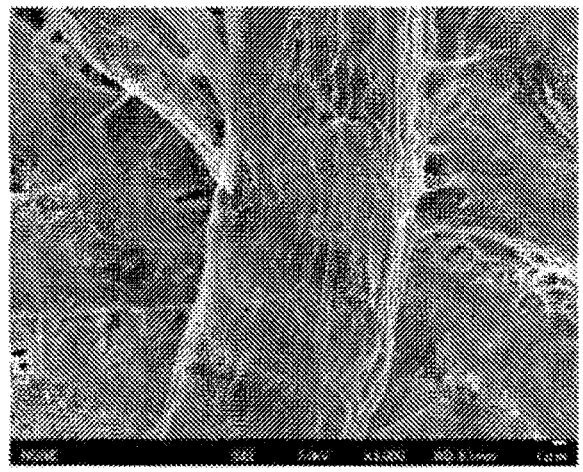
(b) 3000X magnification
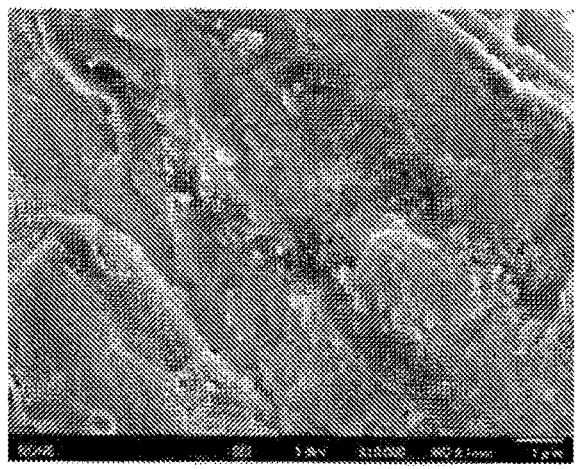
(c) 10000X magnification
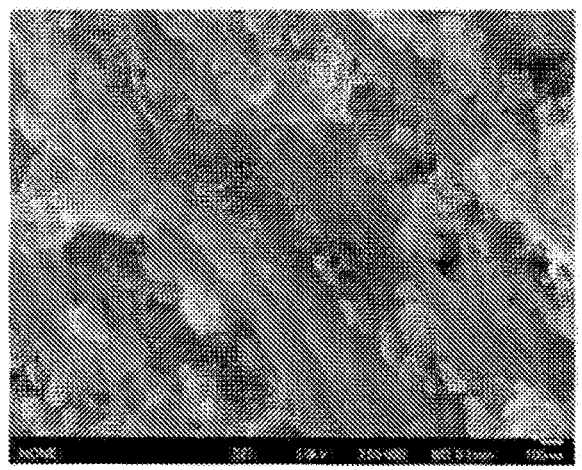
(d) 50000X magnification (a) 500X magnification (b) 3000X magnification (c) 10000X magnification (d) 50000X magnification Fig. 4-5
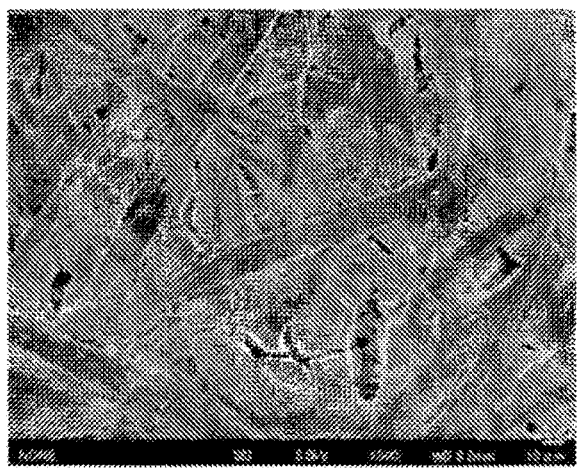
(a) 500X magnification
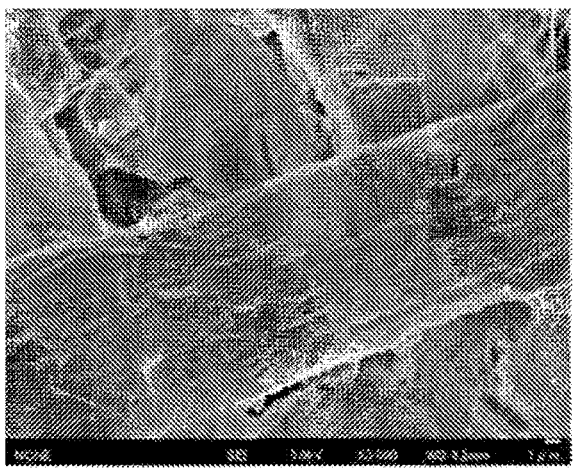
(b) 3000X magnification
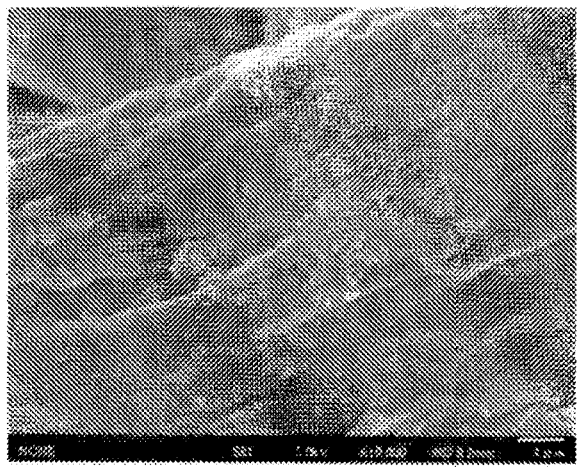
(c) 10000X magnification
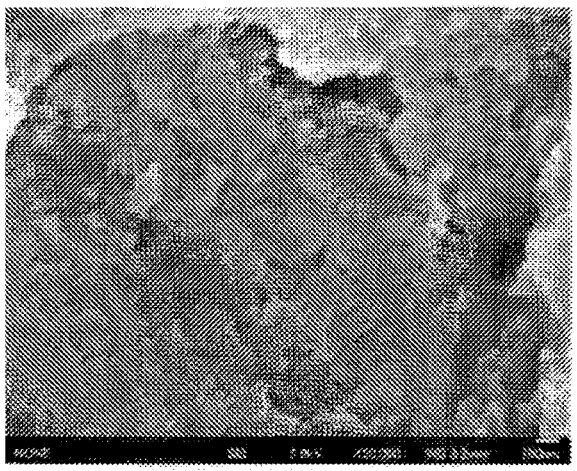
(d) 50000X magnification

COMPLEXES OF HYDROTALCITES AND FIBERS

CROSS-REFERENCE TO RELATED APPLICATIONS

This application is a U.S. national stage filing, under 35 U.S.C. § 371(c), of International Application No. PCT/JP2017/029131, filed on Aug. 10, 2017, which claims priority to Japanese Patent Application No. 2017-003514, filed on Jan. 12, 2017; and Japanese Patent Application No. 2016-158029, filed on Aug. 10, 2016. The entire contents of each of the aforementioned applications are incorporated herein by reference.

TECHNICAL FIELD

The present invention relates to complexes of hydrotalcites and fibers as well as processes for preparing them.

BACKGROUND ART

In general, hydrotalcite is one of compounds represented by general formula $[M^{2+}_{1-x}M^{3+}_{x}(OH)_2][A^{n-}_{x/n} \cdot mH2O]$ wherein $M^{2+}$ represents a divalent metal ion, $M^{3+}$ represents a trivalent metal ion, and $A^{n-}_{x/n}$ represents an interlayer anion, provided that $0<x<1$, n is the valence number of A, and $0 \leq m<1$, and it is used as a catalyst, medicine, additive for resins or the like (PTLs 1 to 3, and NPLs 1 to 3).

Hydrotalcite is a metal hydroxide having a layered crystal structure similarly to talc and smectite, and an individual crystal of hydrotalcite is often foliated or flaky. Hydrotalcite is known to include a polytype of hydrotalcite called manasseite; pyroaurite or sjogrenite wherein the metals contained in the hydroxide sheets are magnesium and iron; green rust containing divalent and trivalent irons in the hydroxide sheets; and the like. It is also called Layered Double Hydroxide (LDH) or the like because its main skeleton consists of a double hydroxide. Hydrotalcite is naturally produced in small amounts, and therefore, it is mostly synthesized and various synthesis methods are known.

PTL 4 proposes deodorant fabrics comprising a polyurethane fiber or the like carrying a metal hydroxide such as hydrotalcite. Further, NPL 4 proposes to remove phosphorus from wastewater using a hydrotalcite-carrying fiber.

CITATION LIST

Patent Literature

PTL 1: JPA 2015-193000
PTL 2: JPA 2013-085568
PTL 3: JPA 2009-143798
PTL 4: JPA 2012-144829

Non-Patent Literature

NPL 1: "Application of hydrotalcite for water environmental preservation and purification", The Chemical Times, no. 1, 2005
NPL 2: "Synthesis and Anion Exchange Properties of Magnesium-Iron (III) and -Aluminum hydrotalcite-like compounds", J. Ion Exchange, vol. 16, no. 1, 2005
NPL 3: "Adsorption Behavior of Layered Double Hydroxide for Surfactants and Structural Stability of Its Emulsion Gel", Journal of Toyo University, Natural Science, No. 56, pp. 43-52, 2012
NPL 4: "Ability to Remove Phosphorus from Wastewater Using Hydrotalcite-Carrying Fiber (HTCF)", Journal of Japan Society on Water Environment, vol. 30, no. 11, pp 671-676, 2007

SUMMARY OF INVENTION

Technical Problem

The present invention aims to provide techniques for efficiently preparing complexes of a hydrotalcite and a fiber.

Solution to Problem

As a result of careful studies about the problems described above, we accomplished the present invention on the basis of the finding that when a hydrotalcite is synthesized in the presence of a fiber, the hydrotalcite forms a stable complex with the fiber.

Thus, the present invention includes, but not limited to, the following:

(1) A process for preparing a complex of a hydrotalcite and a fiber, comprising synthesizing the hydrotalcite in a solution containing the fiber.
(2) The process of (1), comprising the steps of immersing the fiber in an alkaline solution, and then adding an acid solution to the immersed fiber.
(3) The process of (1), comprising the steps of immersing the fiber in an acid solution, and then adding an alkaline solution to the immersed fiber.
(4) The process of any one of (1) to (3), further comprising adding a solution containing an anionic material to the complex of a hydrotalcite and a fiber
(5) The process of any one of (1) to (4), wherein the solution containing an anionic material is a copper- or silver-containing thiosulfato complex solution.
(6) The process of any one of (1) to (5), wherein the fiber is a chemical fiber, a regenerated fiber or a natural fiber.
(7) The process of (6), wherein the fiber is a cellulose fiber.
(8) The process of any one of (1) to (7), wherein the divalent metal ion in the acid solution is magnesium or zinc.
(9) The process of any one of (1) to (8), wherein the trivalent metal ion in the acid solution is aluminum.
(10) The process of any one of (1) to (9), wherein the complex of a hydrotalcite and a fiber contains 10% or more of magnesium or zinc based on the ash content.
(11) A complex comprising a hydrotalcite and a fiber.
(12) The complex of (11), wherein the fiber is a cellulose fiber.
(13) The complex of (11) or (12), wherein 15% or more of the surface of the fiber is covered with the hydrotalcite.
(14) The complex of any one of (11) to (13), wherein the divalent metal ion in the hydrotalcite is magnesium or zinc.
(15) The complex of any one of (11) to (14), wherein the trivalent metal ion in the hydrotalcite is aluminum.
(16) The complex of any one of (11) to (15), comprising copper or silver deposited thereon.
(17) A product comprising the complex of any one of (11) to (16).
(18) The product of (17), which is a sanitary product.
(19) The product of (17) or (18) for use in deodorant applications.
(20) The product of any one of (17) to (19) for use in antibacterial applications.
(21) The product of any one of (17) to (20) for use in antiviral applications.

(22) The product of any one of (17) to (21), which is in the form of a sheet.

Advantageous Effects of Invention

According to the present invention, complexes of a hydrotalcite and a fiber can be obtained. Also, complexes of a hydrotalcite and a fiber providing products having a high retention can be obtained. Further, complexes of a hydrotalcite and a fiber having a high deodorant effect can be obtained

BRIEF DESCRIPTION OF DRAWINGS

FIG. 4-1 shows electron micrographs of a mat (T1) prepared in Experiment 1(3).
FIG. 4-2 shows electron micrographs of a mat (T2) prepared in Experiment 1(3).
FIG. 4-3 shows electron micrographs of a mat (Sample 2) prepared in Experiment 1(3).
FIG. 4-4 shows electron micrographs of a mat (T3) prepared in Experiment 1(3).
FIG. 4-5 shows electron micrographs of a mat (a hydrotalcite-filled paper) prepared in Experiment 1(3).
FIG. 5 shows the results of X-ray diffraction analysis made in Experiment 2.

DESCRIPTION OF EMBODIMENTS

Figure 1:
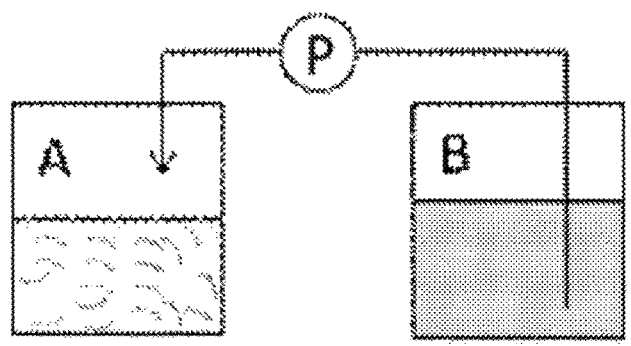
FIG. 1 is a schematic diagram showing a system for preparing Sample 1 in Experiment 1(2).

Complexes of a Hydrotalcite (HT) and a Fiber

In general, hydrotalcite is represented by general formula $[M^{2+}_{1-x}M^{3+}(OH)_2][A^{n-}_{x/n} \cdot mH_2O]$ wherein $M^{2+}$ represents a divalent metal ion, $M^{3+}$ represents a trivalent metal ion, and $A^{n-}_{x/n}$ represents an interlayer anion, provided that $0<x<1$, n is the valence number of A, and $0 \leq m<1$. In the formula above, the divalent metal ion $M^{2+}$ includes, for example, $Mg^{2+}$, $Co^{2+}$, $Ni^{2+}$, $Zn^{2+}$, $Fe^{2+}$, $Ca^+$, $Ba^{2+}$, $Cu^{2+}$, $Mn^{2+}$ and the like; the trivalent metal ion $M^{3+}$ includes, for example, $Al^{3+}$, $Fe^{3+}$, $Cr^{3+}$, $Ga^{3+}$ and the like; the interlayer anion $A^{n-}$ includes, for example, n-valent anions such as $OH^-$, $Cl^-$, $CO_3^-$, $SO_4^-$ and the like; and x is typically in the range of 0.2 to 0.33. Preferably, the divalent metal ion is $Mg^{2+}$, $Zn^{2+}$, $Fe^{2+}$, or $Mn^{2+}$. Its crystal structure is a layered structure consisting of positively charged two-dimensional host layers formed by brucite-like sheets of regular octahedral units and negatively charged interlayers.

Hydrotalcite has been used for various applications taking advantage of its anion exchange function including, for example, ion exchange materials, adsorbents, deodorants and the like. Hydrotalcite has also been used for catalytic applications and the like taking advantage of the combination of component metal ions because a complex oxide having a homogeneous composition can be readily obtained by heating a hydrotalcite having component metal ions in a well-mixed state to dehydrate it or further heating it to calcine it.

The proportion of hydrotalcite in the complexes of the present invention can be 10% or more, or can be 20% or more, or preferably can be 40% or more. The ash content of the complexes of a hydrotalcite and a fiber can be determined according to JIS P 8251: 2003. In the present invention, the ash content of the complexes of a hydrotalcite and a fiber can be 10% or more, or can be 20% or more, or preferably can be 40% or more. Further, the complexes of a hydrotalcite and a fiber of the present invention preferably contain 10% or more, more preferably 40% or more of magnesium, iron, manganese or zinc based on the ash content. The magnesium or zinc level in the ash content can be determined by fluorescent X-ray analysis.

The present invention relates to complexes of a hydrotalcite and a fiber, and in a preferred embodiment, 15% or more of the surface of the fiber is covered with the hydrotalcite. In a preferred embodiment of the complexes of the present invention, the coverage (area ratio) of the fiber by the hydrotalcite is 25% or more, more preferably 40% or more, and complexes having a coverage of 60% or more or even 80% or more can also be prepared according to the present invention. In a preferred embodiment of the complexes of a hydrotalcite and a fiber according to the present invention, the hydrotalcite is not only adhered to the outer surface and the inside of the lumen of the fiber but also can be produced within microfibrils, as proved by electron microscopic observation.

The complexes of a hydrotalcite and a fiber according to the present invention can be formed into products in which the hydrotalcite is not only more readily retained but also uniformly dispersed without being aggregated in contrast to simple mixtures of the hydrotalcite and the fiber. Thus, the complexes of a hydrotalcite and a fiber according to the present invention provide products having a retention (the proportion by weight of the input hydrotalcite remaining in the products) of 65% or more, even 70% or more or 85% or more.

Synthesis of the Complexes of a Hydrotalcite and a Fiber

In the present invention, the complexes of a hydrotalcite and a fiber are prepared by synthesizing the hydrotalcite in a solution in the presence of the fiber.

The hydrotalcite can be synthesized by a known method. For example, a fiber is immersed in an aqueous carbonate solution containing carbonate ions forming interlayers and an alkaline solution (sodium hydroxide or the like) in a reaction vessel, and then an acid solution (an aqueous metal salt solution containing divalent metal ions and trivalent metal ions forming host layers) is added to synthesize a hydrotalcite via a co-precipitation reaction at controlled temperature, pH and the like. Alternatively, a hydrotalcite can also be synthesized via a co-precipitation reaction at controlled temperature, pH and the like by immersing a fiber in an acid solution (an aqueous metal salt solution containing divalent metal ions and trivalent metal ions forming host layers) in a reaction vessel, and then adding dropwise an aqueous carbonate solution containing carbonate ions forming interlayers and an alkaline solution (sodium hydroxide or the like). The reaction typically takes place at ordinary pressure, though a process involving a hydrothermal reaction using an autoclave or the like has also been reported (JPA 1985-6619).

In the present invention, sources of divalent metal ions that can be used for forming host layers include chlorides, sulfides, nitrates and sulfates of magnesium, zinc, barium, calcium, iron, copper, cobalt, nickel, and manganese. Similarly, sources of trivalent metal ions that can be used for forming host layers include chlorides, sulfides, nitrates and sulfates of aluminum, iron, chromium, and gallium.

In the present invention, sources of water that can be used for preparing suspensions or for other purposes include common tap water, industrial water, groundwater, well water and the like, and other sources that can also be conveniently used include ion-exchanged water, distilled water, ultrapure water, industrial waste water, and the water obtained during manufacturing processes.

In the present invention, carbonate ions, nitrate ions, chloride ions, sulfate ions, phosphate ions and the like can be used as interlayer anions. A source of carbonate ions that can be used as interlayer anions includes sodium carbonate. It should be noted that sodium carbonate can be replaced by a gas containing carbon dioxide (carbonic acid gas) including substantially pure carbon dioxide gas or a mixture with another gas. For example, exhaust gases discharged from incinerators, coal-fired boilers, heavy oil-fired boilers and the like in papermaking factories can be conveniently used as gases containing carbon dioxide. Additionally, the carbonation reaction can also be performed using carbon dioxide generated from the lime calcination process.

For preparing the complexes of the present invention, various known auxiliaries can also be added. For example, chelating agents can be added in the neutralization reaction, specifically including polyhydroxycarboxylic acids such as citric acid, malic acid, and tartaric acid; dicarboxylic acids such as oxalic acid; sugar acids such as gluconic acid; aminopolycarboxylic acids such as iminodiacetic acid and ethylenediamine tetraacetic acid and alkali metal salts thereof; alkali metal salts of polyphosphoric acids such as hexametaphosphoric acid and tripolyphosphoric acid; amino acids such as glutamic acid and aspartic acid and alkali metal salts thereof; ketones such as acetylacetone, methyl acetoacetate and allyl acetoacetate; sugars such as sucrose; and polyols such as sorbitol. Surface-treating agents can also be added, including saturated fatty acids such as palmitic acid and stearic acid; unsaturated fatty acids such as oleic acid and linoleic acid; alicyclic carboxylic acids; resin acids such as abietic acid; as well as salts, esters and ethers thereof; alcoholic activators, sorbitan fatty acid esters, amide- or amine-based surfactants, polyoxyalkylene alkyl ethers, polyoxyethylene nonylphenyl ethers, sodium alpha-olefin sulfonate, long-chain alkylamino acids, amine oxides, alkylamines, quaternary ammonium salts, aminocarboxylic acids, phosphonic acids, polycarboxylic acids, condensed phosphoric acids and the like. Further, dispersants can also be used, if desired. Such dispersants include, for example, sodium polyacrylates, sucrose fatty acid esters, glycerol esters of fatty acids, ammonium salts of acrylic acid-maleic acid copolymers, methacrylic acid-naphthoxypolyethylene glycol acrylate copolymers, ammonium salts of methacrylic acid-polyethylene glycol monomethacrylate copolymers, polyethylene glycol monoacrylates and the like. These can be used alone or as a combination of two or more of them. They may be added before or after the neutralization reaction. Such additives can be added preferably in an amount of 0.001 to 20%, more preferably 0.1 to 10% of a hydrotalcite.

(Reaction Conditions)

In the present invention, the temperature of the synthesis reaction can be, for example, 30 to 100° C., preferably 40 to 80° C., more preferably 50 to 70° C., especially preferably about 60° C. If the temperature is excessively high or low, the reaction efficiency decreases and costs tend to increase.

In the present invention, the neutralization reaction can be a batch reaction or a continuous reaction. Typically, the reaction is preferably performed in a batch process because of the convenience in removing residues remaining after the reaction. The scale of the reaction is not specifically limited, and can be 100 L or less, or more than 100 L. The volume of the reaction vessel can be, for example, in the order of 10 L to 100 L, or may be in the order of 100 L to 1000 L.

Further, the neutralization reaction can be controlled by monitoring the pH of the reaction suspension, and the carbonation reaction can be performed until the pH reaches, for example, less than pH 9, preferably less than pH 8, more preferably around pH 7 depending on the pH profile of the reaction suspension.

Alternatively, the neutralization reaction can be controlled by monitoring the conductivity of the reaction suspension. The carbonation reaction is preferably performed until the conductivity decreases to 100 mS/cm or less.

Furthermore, the synthesis reaction can also be controlled by the reaction period, and specifically it can be controlled by adjusting the period during which the reactants stay in the reaction vessel. Additionally, the reaction can also be controlled in the present invention by stirring the reaction suspension in the reaction vessel or performing the neutralization reaction as a multistage reaction.

In the present invention, the reaction product complex is obtained as a suspension so that it can be stored in a storage tank or subjected to processing such as concentration, dehydration, grinding, classification, aging, or dispersion, as appropriate. These can be accomplished by known processes, which may be appropriately selected taking into account the purposes, energy efficiency and the like. For example, the concentration/dehydration process is performed by using a centrifugal dehydrator, thickener or the like. Examples of such centrifugal dehydrators include decanters, screw decanters and the like. If a filter or dehydrator is used, the type of it is not specifically limited either, and those commonly used can be used, including, for example, pressure dehydrators such as filter presses, drum filters, belt presses and tube presses or vacuum drum filters such as Oliver filters or the like, which can be suitably used to give a calcium carbonate cake. Grinding means include ball mills, sand grinder mills, impact mills, high pressure homogenizers, low pressure homogenizers, Dyno mills, ultrasonic mills, Kanda grinders, attritors, millstone type mills, vibration mills, cutter mills, jet mills, breakers, beaters, single screw extruders, twin screw extruders, ultrasonic stirrers, juicers/mixers for home use, etc. Classification means include sieves such as meshes, outward or inward flow slotted or round-hole screens, vibrating screens, heavyweight contaminant cleaners, lightweight contaminant cleaners, reverse cleaners, screening testers and the like. Dispersion means include high speed dispersers, low speed kneaders and the like.

The complexes obtained by the present invention can be compounded as a suspension into fillers or pigments without being completely dehydrated, or can be dried into powders. The dryer used in the latter case is not specifically limited either, but air-flow dryers, band dryers, spray dryers and the like can be suitably used, for example.

The complexes obtained by the present invention can be treated with a weak acid such as dilute hydrochloric acid, dilute nitric acid or the like to intercalate chloride ions or nitrate ions or the like as interlayer ions. Compounds to be intercalated include anionic materials such as copper or silver thiosulfato complexes, for example. Intercalation can be performed by known methods, including adding a solution containing an anionic material to a complex of a hydrotalcite and a fiber and mixing them.

Further, the complexes obtained by the present invention can be modified by known methods. In one embodiment, for example, they can be hydrophobized on their surfaces to enhance the miscibility with resins or the like.

Fibers

In the present invention, a hydrotalcite is complexed with a fiber. The fiber forming part of the complexes is not specifically limited, and examples of fibers that can be used include, without limitation, not only natural fibers such as celluloses but also synthetic fibers artificially synthesized from raw materials such as petroleum, regenerated fibers (semisynthetic fibers) such as rayon and lyocell, and even inorganic fibers such as ceramics and the like. Natural fibers other than the examples mentioned above include protein fibers such as wool and silk yarns and collagen fibers; composite carbohydrate fibers such as chitin/chitosan fibers and alginate fibers and the like.

Examples of cellulosic raw materials include pulp fibers (wood pulps and non-wood pulps), bacterial celluloses, etc., among which wood pulps may be prepared by pulping wood raw materials. Examples of wood raw materials include softwoods such as *Pinus densiflora, Pinus thunbergii, Abies sachalinensis, Picea jezoensis, Pinus koraiensis, Larix kaempferi, Abies firma, Tsuga sieboldii, Cryptomeria japonica, Chamaecyparis obtusa, Larix kaempferi, Abies veitchii, Picea jezoensis* var. *hondoensis, Thujopsis dolabrata*, Douglas fir (*Pseudotsuga menziesii*), hemlock (*Conium maculatum*), white fir (*Abies concolor*), spruces, balsam fir (*Abies balsamea*), cedars, pines, *Pinus merkusii, Pinus radiata*, and mixed materials thereof; and hardwoods such as *Fagus crenata*, birches, *Alnus japonica*, oaks, *Machilus thunbergii, Castanopsis, Betula platyphylla, Populus nigra* var. *italica*, poplars, *Fraxinus, Populus maximowiczii, Eucalyptus*, mangroves, Meranti, Acacia and mixed materials thereof.

The technique for pulping the wood raw materials is not specifically limited, and examples include pulping processes commonly used in the papermaking industry. Wood pulps can be classified by the pulping process and include, for example, chemical pulp obtained by digestion via the kraft process, sulfite process, soda process, polysulfide process or the like; mechanical pulp obtained by pulping with a mechanical force such as a refiner, grinder or the like; semichemical pulp obtained by pulping with a mechanical force after a chemical pretreatment; waste paper pulp; deinked pulp and the like. The wood pulps may have been unbleached (before bleaching) or bleached (after bleaching).

Examples of non-wood pulps include cotton, hemp, sisal (*Agave sisalana*), abaca (*Musa textilis*), flax, straw, bamboo, bagas, kenaf, sugar cane, corn, rice straw, *Broussonetia kazinoki* x *B. papyrifera, Edgeworthia chrysantha* and the like.

The pulp fibers may be unbeaten or beaten depending on the desired properties of complex sheets, but they are preferably beaten. This can be expected to improve the sheet strength and to promote the adhesion of calcium carbonate.

Synthetic fibers include polyesters, polyamides, polyolefins, acrylic fibers, nylon, acrylic fibers, vinylon, ceramic fibers and the like; semisynthetic fibers include rayon, acetate and the like; and inorganic fibers include glass fiber, carbon fiber, various metal fibers and the like.

Moreover, these cellulosic raw materials can be further treated so that they can also be used as powdered celluloses, chemically modified celluloses such as oxidized celluloses, and cellulose nanofibers (CNFs) (microfibrillated celluloses (MFCs), TEMPO-oxidized CNFs, phosphate esters of CNFs, carboxymethylated CNFs, mechanically ground CNFs and the like). Powdered celluloses used in the present invention may be, for example, rod-like crystalline cellulose powders having a certain particle size distribution prepared by purifying/drying and grinding/sieving the undecomposed residue obtained after acid hydrolysis of a cleaned pulp, or may be commercially available products such as KC FLOCK (from Nippon Paper Industries Co., Ltd.), CEOLUS (from Asahi Kasei Chemicals Corp.), AVICEL (from FMC Corporation) and the like. The degree of polymerization of celluloses in the powdered celluloses is preferably in the order of 100 to 1500, and the powdered celluloses preferably have a crystallinity of 70 to 90% as determined by X-ray diffraction and also preferably have a volume average particle size of 1 µm or more and 100 µm or less as determined by a laser diffraction particle size distribution analyzer. Oxidized celluloses used in the present invention can be obtained by oxidation with an oxidizing agent in water in the presence of an N-oxyl compound and a compound selected from the group consisting of a bromide, an iodide or a mixture thereof, for example. Cellulose nanofibers can be obtained by disintegrating the cellulosic raw materials mentioned above. Disintegration methods that can be used include, for example, mechanically grinding or beating an aqueous suspension or the like of a cellulose or a chemically modified cellulose such as an oxidized cellulose using a refiner, high pressure homogenizer, grinder, single screw or multi-screw kneader, bead mill or the like. Cellulose nanofibers may be prepared by using one or a combination of the methods described above. The fiber diameter of the cellulose nanofibers thus prepared can be determined by electron microscopic observation or the like and falls within the range of, for example, 5 nm to 1000 nm, preferably 5 nm to 500 nm, more preferably 5 nm to 300 nm. During the preparation of the cellulose nanofibers, a given compound can be further added before and/or after the celluloses are disintegrated and/or micronized, whereby it reacts with the cellulose nanofibers to functionalize the hydroxyl groups. Functional groups used for the functionalization include acyl groups such as acetyl, ester, ether, ketone, formyl, benzoyl, acetal, hemiacetal, oxime, isonitrile, allene, thiol, urea, cyano, nitro, azo, aryl, aralkyl, amino, amide, imide, acryloyl, methacryloyl, propionyl, propioloyl, butyryl, 2-butyryl, pentanoyl, hexanoyl, heptanoyl, octanoyl, nonanoyl, decanoyl, undecanoyl, dodecanoyl, myristoyl, palmitoyl, stearoyl, pivaloyl, benzoyl, naphthoyl, nicotinoyl, isonicotinoyl, furoyl and cinnamoyl; isocyanate groups such as 2-methacryloyloxtyethyl isocyanoyl; alkyl groups such as methyl, ethyl, propyl, 2-propyl, butyl, 2-butyl, tert-butyl, pentyl, hexyl, heptyl, octyl, nonyl, decyl, undecyl, dodecyl, myristyl, palmityl, and stearyl; oxirane, oxetane, oxyl, thiirane, thietane and the like. Hydrogens in these substituents may be substituted by a functional group such as hydroxyl or carboxyl. Further, the alkyl groups may be partially unsaturated with an unsaturated bond. Compounds used for introducing these functional groups are not specifically limited and include, for example, compounds containing phosphate-derived groups, compounds containing carboxylate-derived groups, compounds containing sulfate-derived groups, compounds containing sulfonate-derived groups, compounds containing alkyl groups, compounds containing amine-derived groups and the like. Phosphate-containing compounds include, but not specifically limited to, phosphoric acid and lithium salts of phosphoric acid such as lithium dihydrogen phosphate, dilithium hydrogen phosphate, trilithium phosphate, lithium pyrophosphate, and lithium polyphosphate. Other examples include sodium salts of phosphoric acid such as sodium dihydrogen phosphate, disodium hydrogen phosphate, trisodium phosphate, sodium pyrophosphate, and sodium polyphosphate. Further examples include potassium salts of phosphoric acid such as potassium dihydrogen phosphate, dipotassium hydrogen phosphate, tripotassium phosphate, potassium pyrophosphate, and potassium polyphosphate. Still further examples include ammonium salts of phosphoric acid such as ammonium dihydrogen phosphate, diammonium hydrogen phosphate, triammonium phosphate, ammonium pyrophosphate, ammonium polyphosphate and the like. Among them, preferred are, but not specifically limited to, phosphoric acid, sodium salts of phosphoric acid, potassium salts of phosphoric acid, and ammonium salts of phosphoric acid, and more preferred are sodium dihydrogen phosphate and disodium hydrogen phosphate because they allow phosphate groups to be introduced with high efficiency so that they are convenient for industrial applications. Carboxyl-containing compounds include, but not specifically limited to, dicarboxylic compounds such as maleic acid, succinic acid, phthalic acid, fumaric acid, glutaric acid, adipic acid, and itaconic acid; and tricarboxylic compounds such as citric acid, and aconitic acid. Acid anhydrides of carboxyl-containing compounds include, but not specifically limited to, acid anhydrides of dicarboxylic compounds such as maleic anhydride, succinic anhydride, phthalic anhydride, glutaric anhydride, adipic anhydride, and itaconic anhydride. Derivatives of carboxyl-containing compounds include, but not specifically limited to, imides of acid anhydrides of carboxyl-containing compounds, and derivatives of acid anhydrides of carboxyl-containing compounds. Imides of acid anhydrides of carboxyl-containing compounds include, but not specifically limited to, imides of dicarboxylic compounds such as maleimide, succinimide, and phthalimide. Derivatives of acid anhydrides of carboxyl-containing compounds are not specifically limited. For example, they include acid anhydrides of carboxyl-containing compounds in which hydrogen atoms are at least partially substituted by a substituent (e.g., alkyl, phenyl or the like) such as dimethylmaleic anhydride, diethylmaleic anhydride, and diphenylmaleic anhydride. Among the compounds containing carboxylate-derived groups mentioned above, preferred are, but not specifically limited to, maleic anhydride, succinic anhydride and phthalic anhydride because they are convenient for industrial applications and can be readily gasified. Further, these compounds may be physically adsorbed rather than chemically bonded to the cellulose nanofibers to functionalize the cellulose nanofibers. Physically adsorbed compounds include surfactants, which may be anionic, cationic, or nonionic. When celluloses are functionalized as described above before they are disintegrated and/or ground, these functional groups can be removed, giving back the original hydroxyl groups after they are disintegrated and/or ground. The functionalization as described above can promote disintegration into cellulose nanofibers or help cellulose nanofibers to be mixed with various materials during use.

The fibers shown above may be used alone or as a mixture of two or more of them. Especially, the complexes preferably comprise a wood pulp or a combination of a wood pulp with a non-wood pulp and/or a synthetic fiber, more preferably a wood pulp alone.

In preferred embodiments, the fiber forming part of the complexes of the present invention is a pulp fiber. Alternatively, fibrous materials collected from waste water of papermaking factories may be used in the present invention, for example. Various composite particles including those of various shapes such as fibrous particles can be synthesized by supplying such materials to the reaction vessel.

Molded Products of the Complexes

The complexes of the present invention can be used to prepare molded products, as appropriate. For example, the complexes obtained by the present invention can be readily formed into sheets having a high ash content. Paper machines (sheet-forming machines) used for preparing sheets include, for example, Fourdrinier machines, cylinder machines, gap formers, hybrid formers, multilayer paper machines, known sheet-forming machines combining the papermaking methods of these machines and the like. The linear pressure in the press section of the paper machines and the linear calendering pressure in a subsequent optional calendering process can be both selected within a range convenient for the runnability and the performance of the complex sheets. Further, the sheets thus formed may be impregnated or coated with starches, various polymers, pigments and mixtures thereof.

During sheet forming, wet and/or dry strength additives (paper strength additives) can be added. This allows the strength of the complex sheets to be improved. Strength additives include, for example, resins such as urea-formaldehyde resins, melamine-formaldehyde resins, polyamides, polyamines, epichlorohydrin resins, vegetable gums, latexes, polyethylene imines, glyoxal, gums, mannogalactan polyethylene imines, polyacrylamide resins, polyvinylamines, and polyvinyl alcohols; composite polymers or copolymers composed of two or more members selected from the resins mentioned above; starches and processed starches; carboxymethylcellulose, guar gum, urea resins and the like. The amount of the strength additives to be added is not specifically limited.

Further, high molecular weight polymers or inorganic materials can be added to promote the adhesion of fillers to fibers or to improve the retention of fillers or fibers. For example, coagulants can be added, including cationic polymers such as polyethylene imines and modified polyethylene imines containing a tertiary and/or quaternary ammonium group, polyalkylene imines, dicyandiamide polymers, polyamines, polyamine/epichlorohydrin polymers, polymers of dialkyldiallyl quaternary ammonium monomers, dialkylaminoalkyl acrylates, dialkylaminoalkyl methacrylates, dialkylaminoalkyl acrylamides and dialkylaminoalkyl methacrylamides with acrylamides, monoamine/epihalohydrin polymers, polyvinylamines and polymers containing a vinylamine moiety as well as mixtures thereof; cation-rich zwitterionic polymers containing an anionic group such as a carboxyl or sulfone group copolymerized in the molecules of the polymers mentioned above; mixtures of a cationic polymer and an anionic or zwitterionic polymer and the like.

Further, retention aids such as cationic or anionic or zwitterionic polyacrylamide-based materials can be used. These may be applied as retention systems called dual polymers in which they are used in combination with at least one or more cationic or anionic polymers, or may be applied as multi-component retention systems in which they are used in combination with at least one or more anionic inorganic microparticles such as bentonite, colloidal silica, polysilicic acid, microgels of polysilicic acid or polysilicic acid salts and aluminum-modified products thereof or one or more organic microparticles having a particle size of 100 μm or less called micropolymers composed of crosslinked/polymerized acrylamides. Especially when the polyacrylamide-based materials used alone or in combination with other materials have a weight-average molecular weight of 2,000,000 Da or more, preferably 5,000,000 Da or more as determined by intrinsic viscosity measurement, good retention can be achieved, and when the acrylamide-based materials have a molecular weight of 10,000,000 Da or more and less than 30,000,000 Da, very high retention can be achieved. The polyacrylamide-based materials may be in the form of an emulsion or solution. Specific compositions of such materials are not specifically limited so far as they contain an acrylamide monomer unit as a building block therein, but include, for example, copolymers of a quaternary ammonium salt of an acrylate ester and an acrylamide, or ammonium salts obtained by copolymerizing an acrylamide and an acrylate ester and then quaternarizing the copolymer. The cationic charge density of the cationic polyacrylamide-based materials is not specifically limited.

Other additives include freeness improvers, internal sizing agents, pH modifiers, antifoaming agents, pitch control agents, slime control agents, bulking agents, inorganic particles (the so-called fillers) such as calcium carbonate, kaolin, talc and silica and the like depending on the purposes. The amount of these additives to be used is not specifically limited.

Molding techniques other than sheet forming may also be used, and molded products having various shapes can be obtained by the so-called pulp molding process involving casting a raw material into a mold and then dewatering by suction and drying it or the process involving spreading a raw material over the surface of a molded product of a resin or metal or the like and drying it, and then releasing the dried material from the substrate or other processes. Further, the complexes can be molded like plastics by mixing them with resins, or can be molded like ceramics by calcining them with minerals such as silica or alumina. In the compounding/drying/molding steps shown above, only one complex can be used, or a mixture of two or more complexes can be used. Two or more complexes can be used as a premixture of them or can be mixed after they have been individually compounded, dried and molded.

During the preparation of molded products using the complexes of the present invention, various organic materials such as polymers or various inorganic materials such as pigments or various fibers such as pulp fibers may be added. Further, various organic materials such as polymers or various inorganic materials such as pigments or various fibers such as pulp fibers may be added later to molded products of the complexes.

The complexes obtained by the present invention can be used for various applications including, for example, papers, fibers, cellulosic composite materials, filter materials, paints, plastics and other resins, rubbers, elastomers, ceramics, glasses, tires, construction materials (asphalt, asbestos, cement, boards, concrete, bricks, tiles, plywoods, fiber boards and the like), various carriers (catalyst carriers, drug carriers, agrochemical carriers, microbial carriers and the like), adsorbents (decontaminants, deodorants, dehumidifying agents and the like), anti-wrinkle agents, clays, abrasives, modifiers, repairing materials, thermal insulation materials, damp proofing materials, water repellent materials, waterproofing materials, light shielding materials, sealants, shielding materials, insect repellents, adhesives, inks, cosmetics, medical materials, paste materials, food additives, tablet excipients, dispersants, structuring agents, water retention agents, filter aids, oil rectification additives, oil processing additives, oil reforming additives, electromagnetic wave absorbers, insulating materials, acoustic insulation materials, vibration damping materials, semiconductor sealing materials, radiation shielding materials, cosmetics, fertilizers, feedstuffs, perfumes, additives for paints, adhesives and resins, discoloration inhibitors, electrically conductive materials, thermally conductive materials, sanitary products (disposable diapers, sanitary napkins, incontinence pads, nursing pads), etc., thus they can be widely used for any applications. They also can be used for various fillers, coating agents and the like in the applications mentioned above. Among them, they are preferably used for adsorbents (decontaminants, deodorants, dehumidifying agents and the like), and sanitary products (disposable diapers, sanitary napkins, incontinence pads, nursing pads).

The complexes of the present invention may also be applied for papermaking purposes including, for example, printing papers, newsprint papers, inkjet printing papers, PPC papers, kraft papers, woodfree papers, coated papers, coated fine papers, wrapping papers, thin papers, colored woodfree papers, cast-coated papers, carbonless copy papers, label papers, heat-sensitive papers, various fancy papers, water-soluble papers, release papers, process papers, hanging base papers, incombustible papers, flame retardant papers, base papers for laminated boards, printed electronics papers, battery separators, cushion papers, tracing papers, impregnated papers, papers for ODP, building papers, papers for decorative building materials, envelope papers, papers for tapes, heat exchange papers, chemical fiber papers, aseptic papers, water resistant papers, oil resistant papers, heat resistant papers, photocatalytic papers, cosmetic papers (facial blotting papers and the like), various sanitary papers (toilet papers, facial tissues, wipers, diapers, menstrual products and the like), cigarette rolling papers, paperboards (liners, corrugating media, white paperboards and the like), base papers for paper plates, cup papers, baking papers, abrasive papers, synthetic papers and the like.

EXAMPLES

The following examples further illustrate the present invention, but the present invention is not limited to these examples. Unless otherwise specified, the concentrations, parts and the like as used herein are based on weight, and the numerical ranges are described to include their endpoints.

Experiment 1: Complexes of a Hydrotalcite and a Fiber (1) Preparation of an Alkaline Solution and Acid Solutions Solutions for synthesizing hydrotalcites (HTs) were prepared. An aqueous mixed solution of $Na_2CO_3$ (Wako Pure Chemical Industries, Ltd.) and NaOH (Wako Pure Chemical Industries, Ltd.) was prepared as an alkaline solution (solution A). On the other hand, an aqueous mixed solution of $MgCl_2$ (Wako Pure Chemical Industries, Ltd.) and $AlCl_3$ (Wako Pure Chemical Industries, Ltd.) and an aqueous mixed solution of $ZnCl_2$ (Wako Pure Chemical Industries, Ltd.) and $AlCl_3$ (Wako Pure Chemical Industries, Ltd.) were prepared as acid solutions (solutions B).

Alkaline solution (solution A; $Na_2CO_3$ concentration 0.05 M; NaOH concentration 0.8 M);
Acid solution (solution B, Mg-based; $MgCl_2$ concentration 0.3 M; $AlCl_3$ concentration 0.1 M);
Acid solution (solution B, Zn-based; $ZnCl_2$ concentration 0.3 M; $AlCl_3$ concentration 0.1 M).

(2) Synthesis of Complexes (Sample 0: $Mg_6Al_2(OH)_{16}CO_3 \cdot 4H_2O$)

A 10-L reaction vessel was charged with the alkaline solution, and the acid solution (Mg-based) was added dropwise with stirring to synthesize hydrotalcite microparticles. The reaction temperature was 60° C., the dropwise addition rate was 15 ml/min, and when the pH of the reaction solution reached about 7, the dropwise addition was stopped. After completion of the dropwise addition, the reaction solution was stirred for 30 minutes, and washed with about 10 volumes of water to remove the salt.

(Sample 1: A Complex of $Mg_6Al_2(OH)_{16}CO_3 \cdot 4H_2O$ and a Pulp Fiber)

A cellulose fiber was used as the fiber to be complexed. Specifically, a pulp fiber was used, which comprises a bleached hardwood kraft pulp (LBKP from Nippon Paper Industries Co., Ltd.) and a bleached softwood kraft pulp (NBKP from Nippon Paper Industries Co., Ltd.) in a weight ratio of 8:2 and which has been processed to a Canadian standard freeness of 390 ml using a single disc refiner (SDR).

The pulp fiber was added to the alkaline solution to prepare an aqueous suspension containing the pulp fiber (having a pulp fiber consistency of 1.56% at about pH 12.4). A 10-L reaction vessel was charged with this aqueous suspension (pulp solids 30 g), and the acid solution (Mg-based) was added dropwise while stirring the aqueous suspension to synthesize a complex of hydrotalcite microparticles and the fiber. The system as shown in FIG. 1 was used at a reaction temperature of 60° C. and a dropwise addition rate of 15 ml/min, and when the pH of the reaction suspension reached about 7, the dropwise addition was stopped. After completion of the dropwise addition, the reaction suspension was stirred for 30 minutes, and washed with about 10 volumes of water to remove the salt.

(Sample 2: A Complex of $Mg_6Al_2(OH)_{16}CO_3 \cdot 4H_2O$ and a Pulp Fiber)

A complex was prepared in the same manner as described for Sample 1 except that the alkaline solution and the acid solution (Mg-based) were added in reverse order. The pH of the aqueous suspension before the dropwise addition was about 2.8, and when the pH of the reaction suspension reached about 7, the dropwise addition of the alkaline solution was stopped.

(Sample 3: A Complex of $Zn_6Al_2(OH)_{16}CO_3 \cdot 4H_2O$ and a Pulp Fiber)

A complex was prepared in the same manner as described for Sample 1 except that the acid solution (solution B) used was the Zn-based solution. The pH of the aqueous suspension before the dropwise addition was about 12.3, and when the pH of the reaction suspension reached about 6.5, the dropwise addition of the acid solution (Zn-based) was stopped.

(Sample 4: A Complex of Calcium Carbonate and a Pulp Fiber)

A complex of calcium carbonate and a pulp fiber was prepared in the same manner as described in Experiment 1 of JPA 2015-199655. Thus, calcium carbonate was synthesized in an aqueous system in the presence of a hardwood pulp fiber (a CV-treated pulp) to prepare a complex of calcium carbonate and the pulp fiber.

(Sample 5: A Complex of Magnesium Carbonate and a Pulp Fiber)

A 45-L cavitation system was charged with 14 L of an aqueous suspension containing 140 g of magnesium hydroxide (Wako Pure Chemical Industries, Ltd.) and 140 g of a bleached hardwood kraft pulp (LBKP having a CSF of 370 ml and an average fiber length of 0.75 mm), and carbonic acid gas was injected into the reaction vessel while circulating the reaction suspension to synthesize a complex of magnesium carbonate microparticles and the fiber by the carbonation process. The reaction temperature was about 36° C., the carbonic acid gas source was a commercially available liquefied gas, and the injection flow rate of the carbonic acid gas was 4 L/min. When the pH of the reaction suspension reached about 8 (from the pH of about 9.5 before the reaction), the injection of $CO_2$ was stopped, after which the generation of cavitation and the circulation of the slurry in the system were continued for 30 minutes to give a complex of magnesium carbonate and the pulp fiber.

Figure 2:
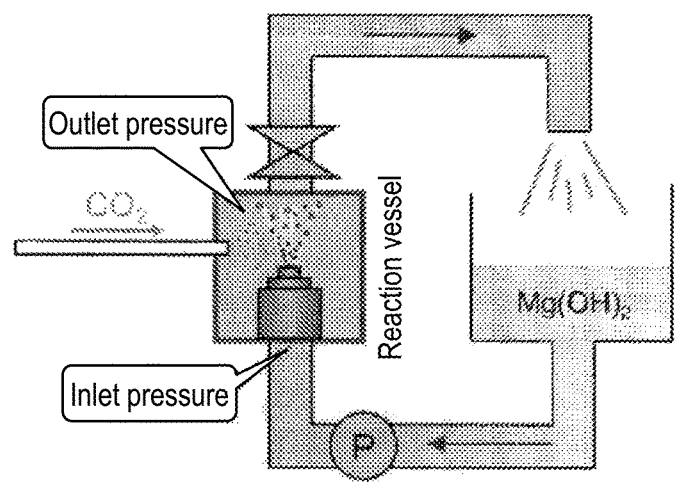
FIG. 2 is a schematic diagram showing a system for preparing Sample 5 in Experiment 1(2).

During the synthesis of the complex, cavitation bubbles were generated in the reaction vessel by injecting the reaction suspension into the reaction vessel while circulating it, as shown in FIG. 2. Specifically, cavitation bubbles were generated by injecting the reaction suspension through a nozzle (having a nozzle diameter of 1.5 mm) under high pressure. The injection rate was about 70 m/s, the inlet pressure (upstream pressure) was 1.8 MPa, and the outlet pressure (downstream pressure) was 0.3 MPa.

(3) Evaluation of the Complexes

Each complex synthesized was used to prepare a mat (having a basis weight of about 100 g/m$^2$) according to JIS P 8222. Specifically, an aqueous slurry (about 0.5%) of the complex was filtered through a filter paper (Class 5B for quantitative analysis as defined by JIS P3801), and the resulting sample was dehydrated under a pressure of 1 MPa for 5 minutes, and then dried under tension at 50° C. for 2 hours to prepare a complex mat having a size of about 200 cm$^2$. As controls, a mat formed of pulp alone (T1) and a mat internally filled with a hydrotalcite (hereinafter referred to as "hydrotalcite-filled paper") were also prepared. The mat formed of pulp alone and the hydrotalcite-filled paper were prepared according to JIS P 8222 from an aqueous slurry (about 0.5%) of the LBKP/NBKP pulp mixture (CSF 390 ml) and a suspension containing a hydrotalcite (Sample 0) in an aqueous slurry (about 0.5%) of the LBKP/NBKP pulp mixture (CSF 390 ml), respectively.

Figure 3:
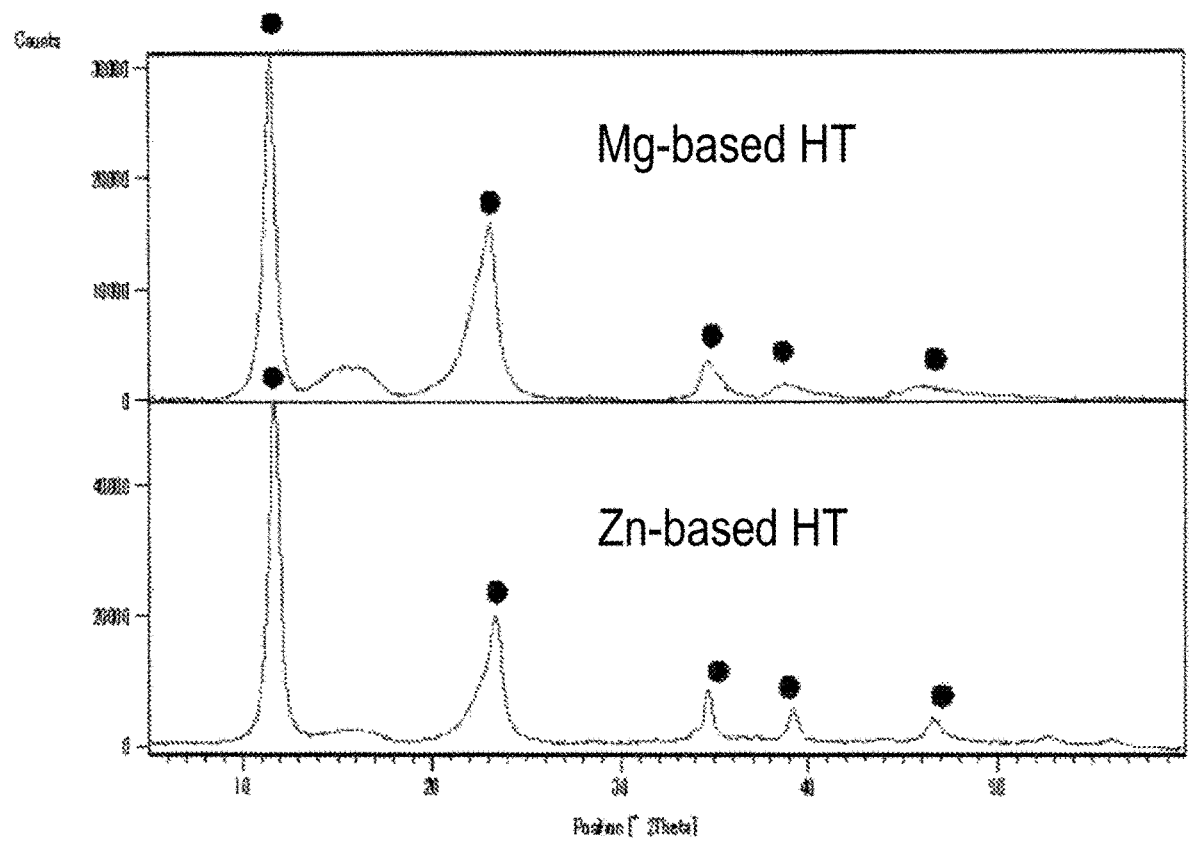
FIG. 3 shows the results of X-ray diffraction analysis made in Experiment 1(3).

Sample 1 (Mg-based HT) and Sample 3 (Zn-based HT) were analyzed by X-ray diffraction to identify hydrotalcite-derived peaks (FIG. 3, solid circles).

Figure 4:
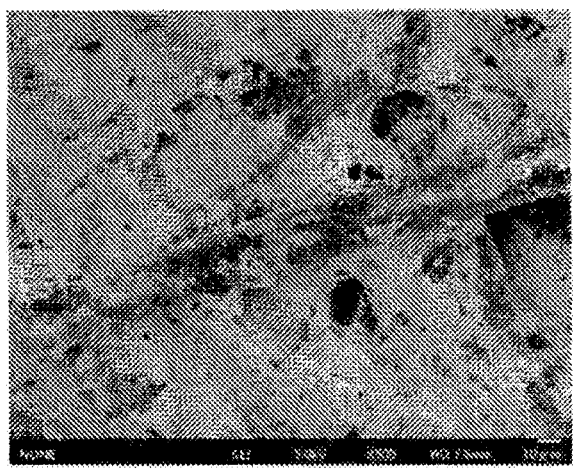
Figure 4:
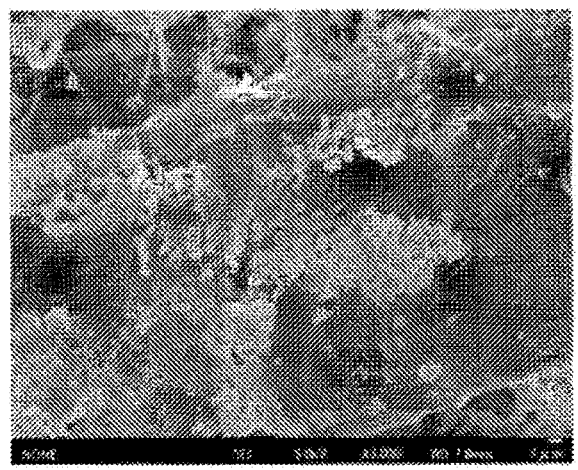
Figure 4:
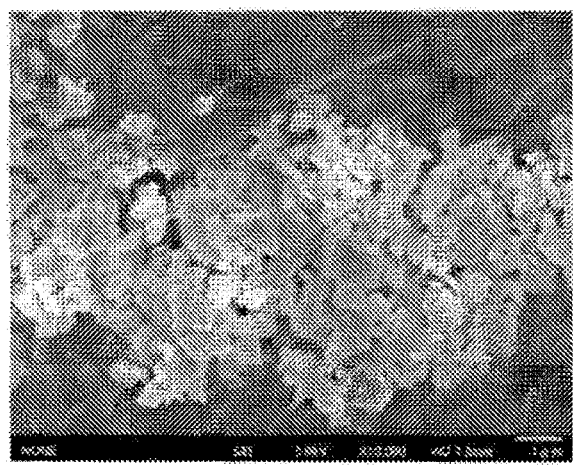
Figure 4:
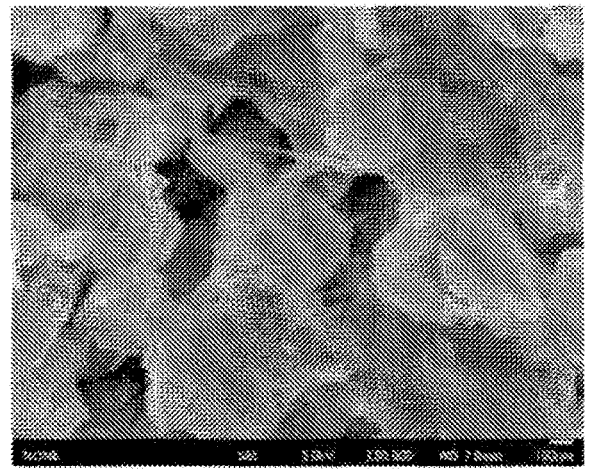
Figure 5:
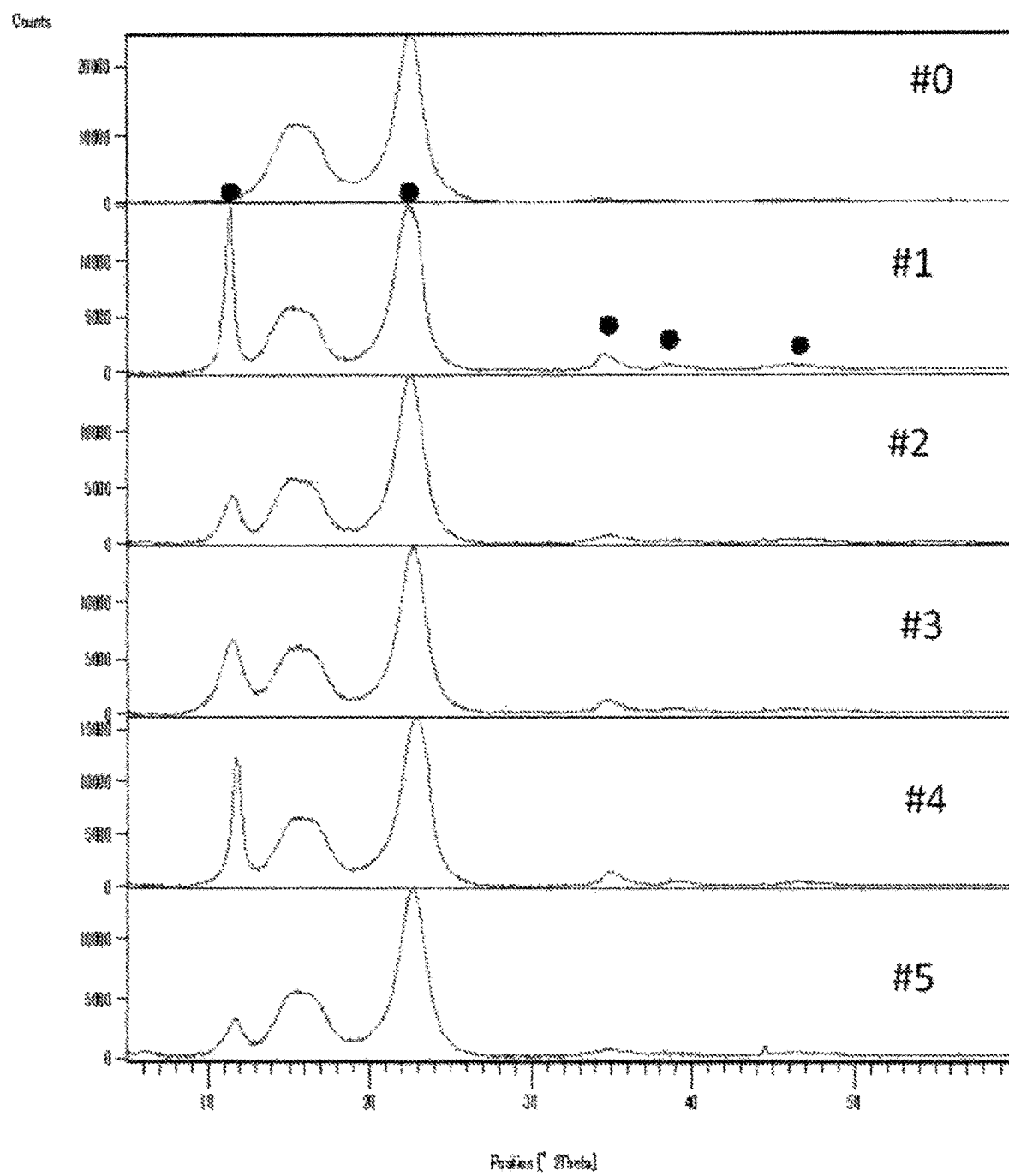
Figure 6:
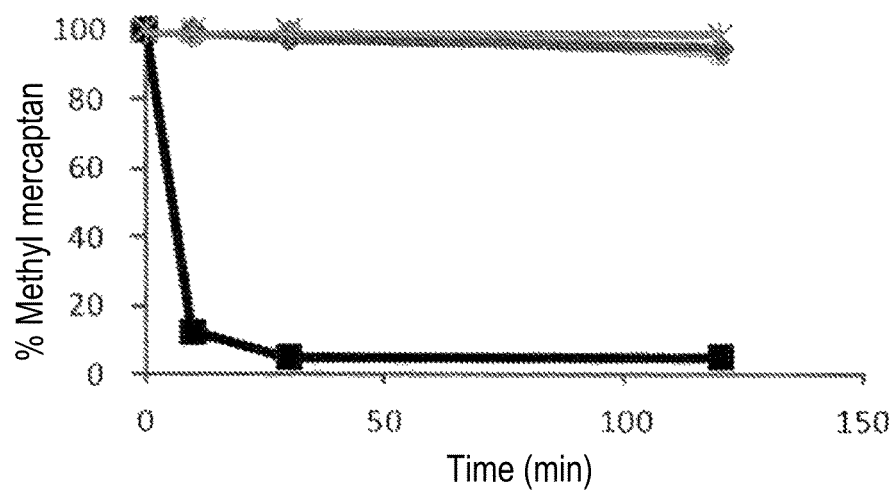
FIG. 6 provides graphs showing the results of the deodorant test in Experiment 3 (methyl mercaptan; upper panel: dry condition; lower panel: wet condition).
Figure 6:
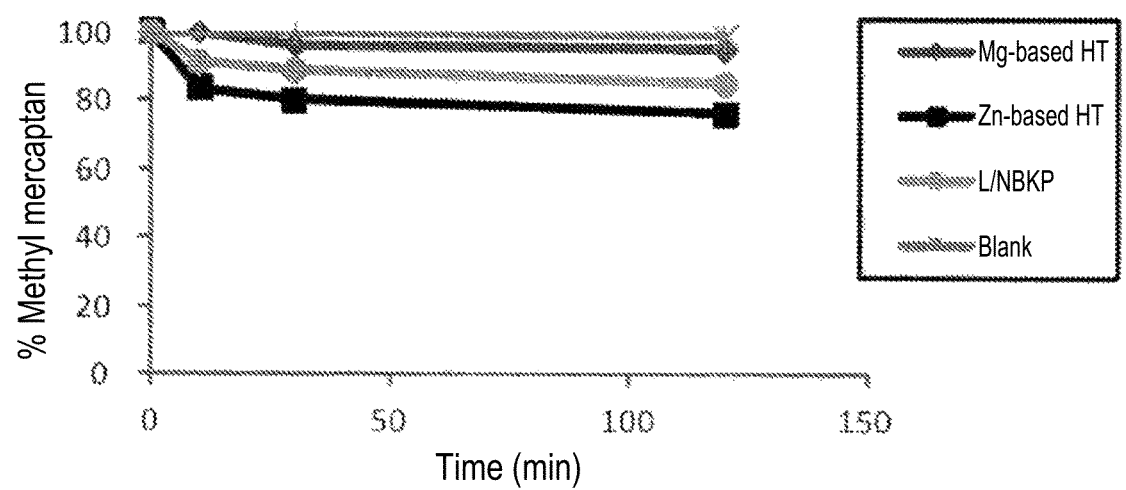
Figure 7:
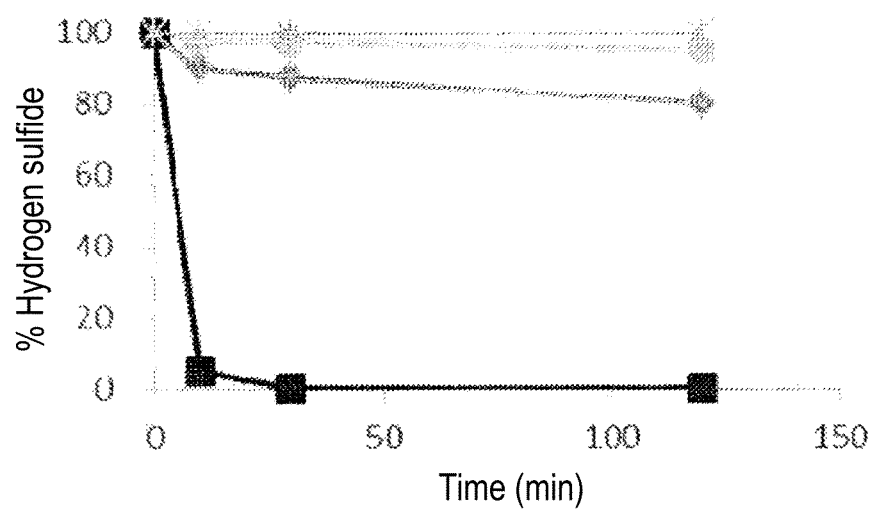
FIG. 7 provides graphs showing the results of the deodorant test in Experiment 3 (hydrogen sulfide; upper panel: dry condition; lower panel: wet condition).
Figure 7:
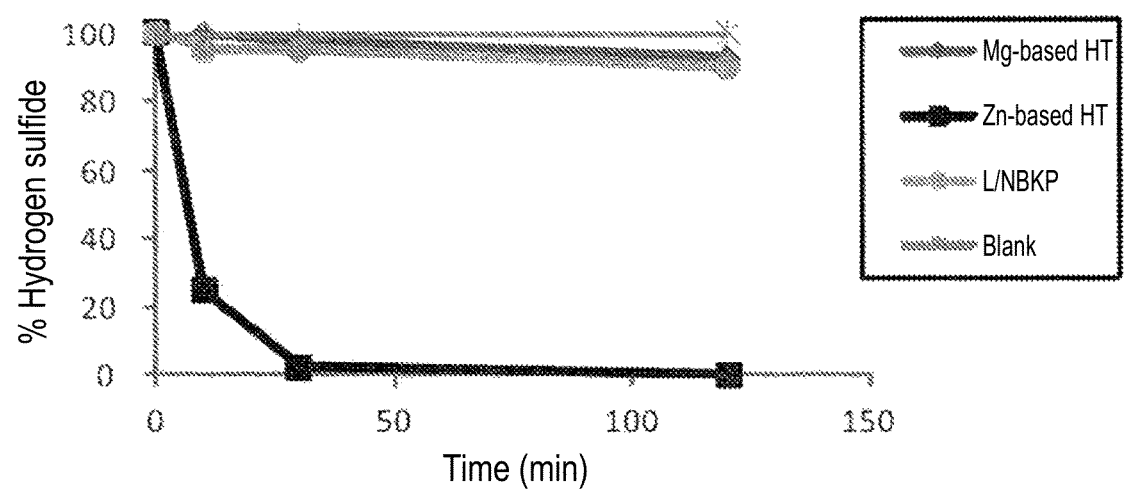
Figure 8:
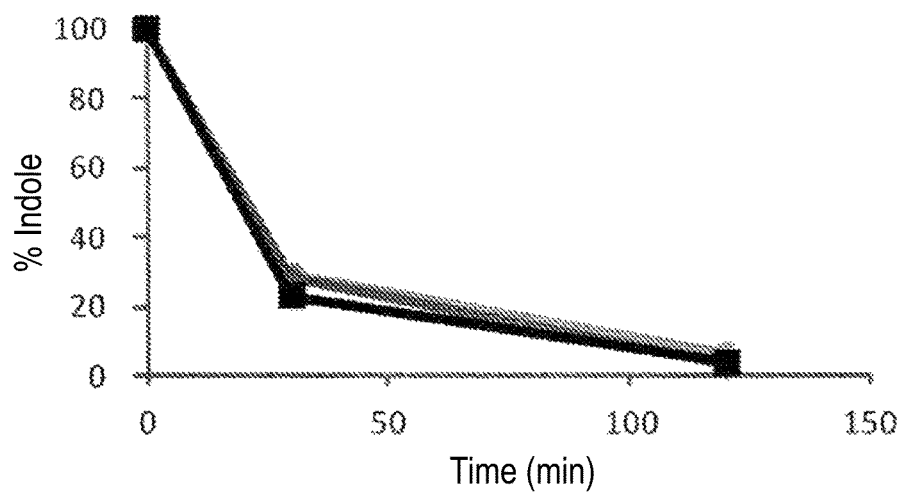
FIG. 8 provides graphs showing the results of the deodorant test in Experiment 3 (indole; upper panel: dry condition; lower panel: wet condition).
Figure 8:
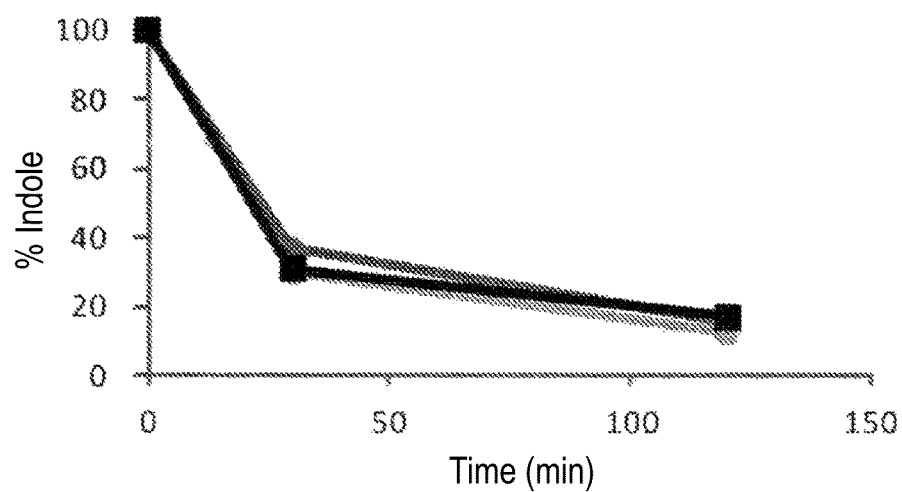
Figure 9:
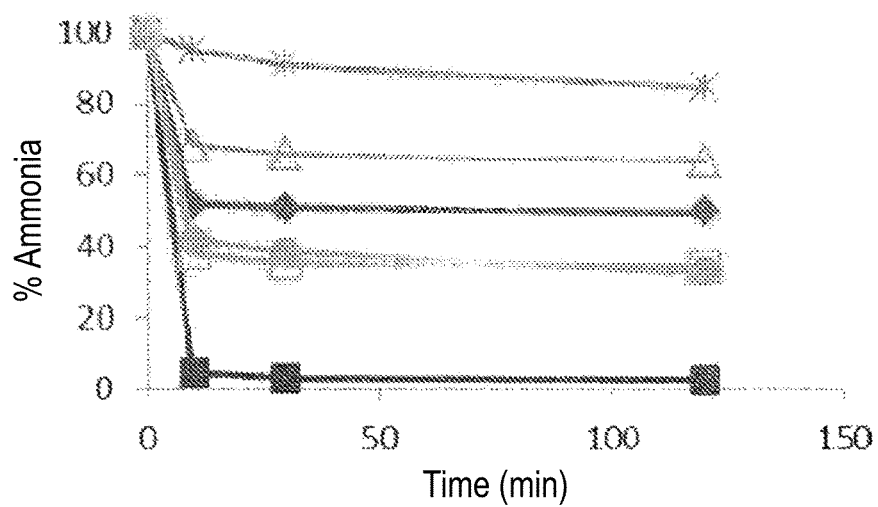
FIG. 9 provides graphs showing the results of the deodorant test in Experiment 3 (ammonia; upper panel: dry condition; lower panel: wet condition).
Figure 9:
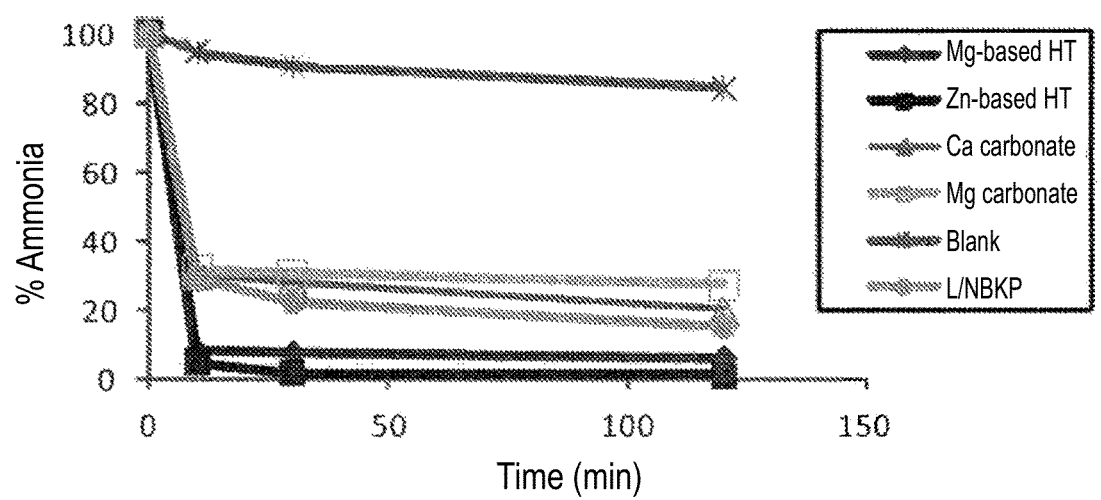
Figure 10:
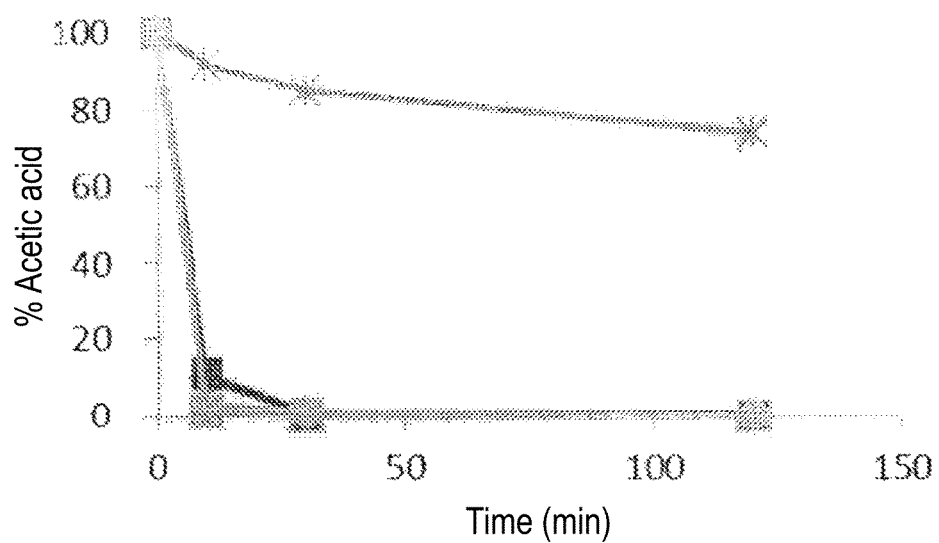
FIG. 10 provides graphs showing the results of the deodorant test in Experiment 3 (acetic acid; upper panel: dry condition; lower panel: wet condition).
Figure 10:
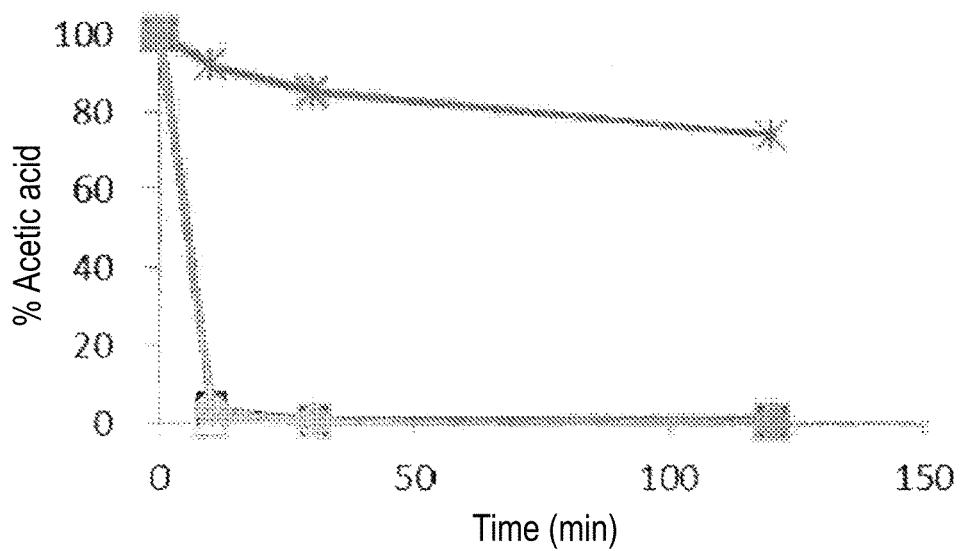
Figure 11:
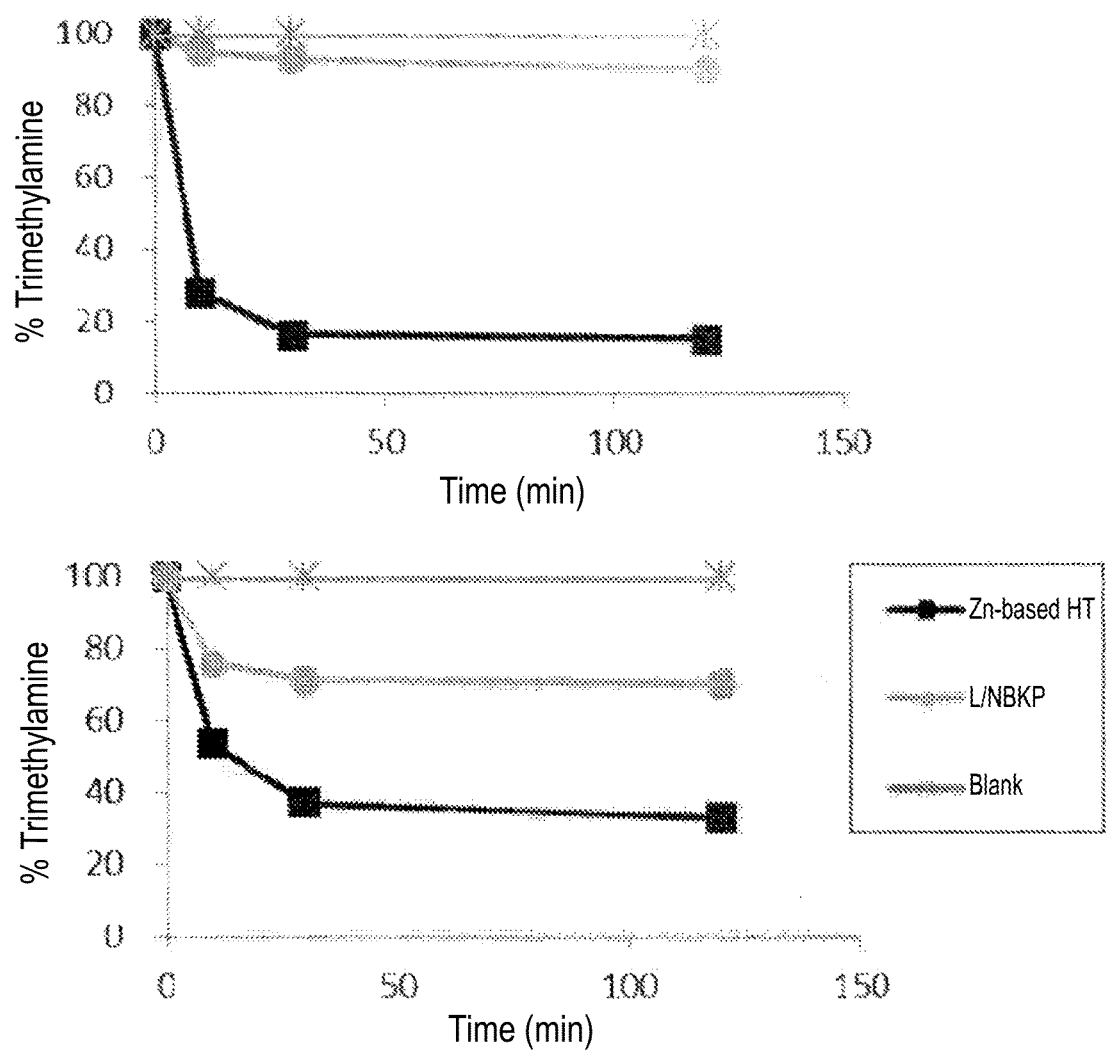
FIG. 11 provides graphs showing the results of the deodorant test in Experiment 3 (trimethylamine; upper panel: dry condition; lower panel: wet condition).
Figure 12:
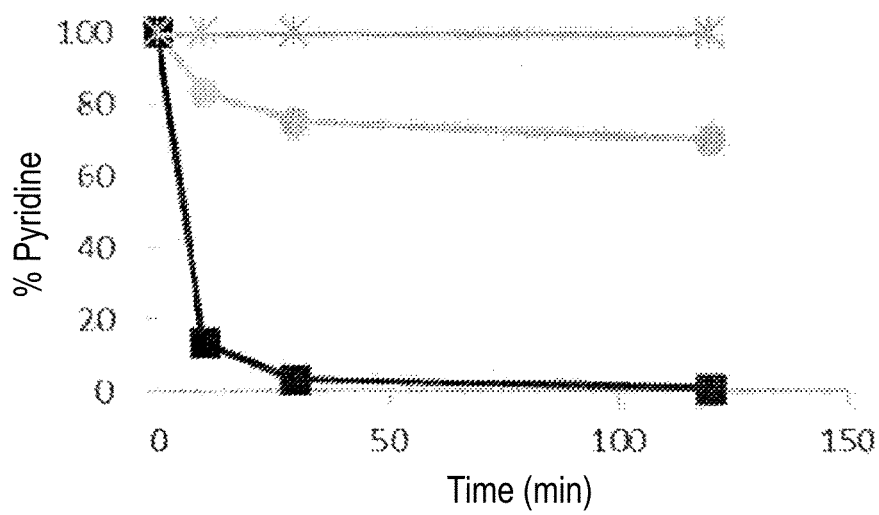
FIG. 12 provides graphs showing the results of the deodorant test in Experiment 3 (pyridine; upper panel: dry condition; lower panel: wet condition).
Figure 12:
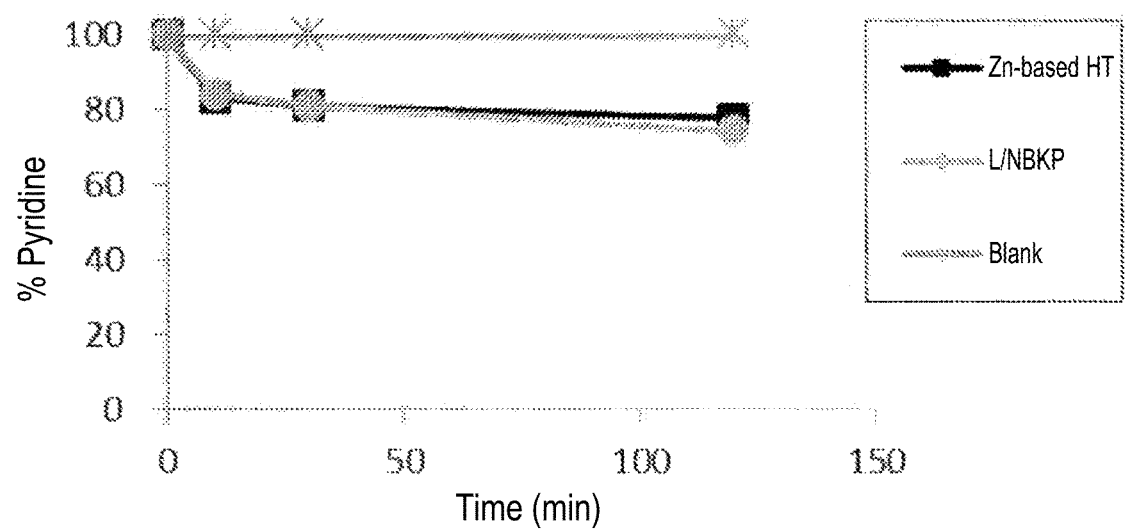
Figure 13:
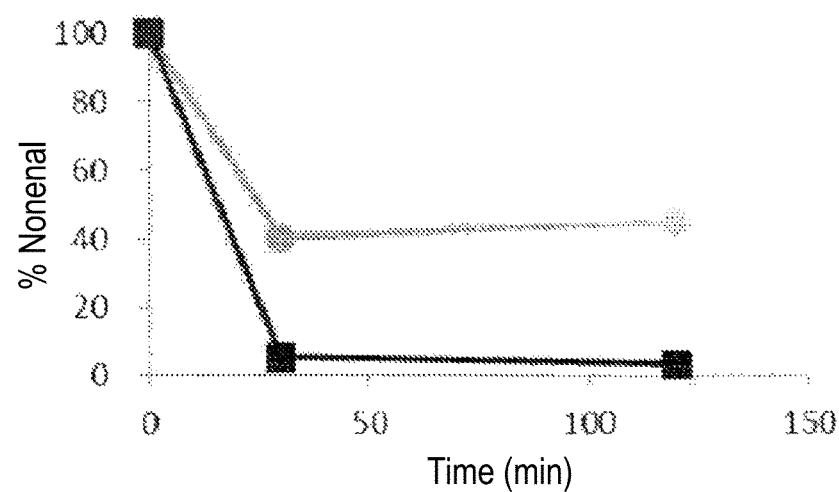
FIG. 13 provides graphs showing the results of the deodorant test in Experiment 3 (nonenal; upper panel: dry condition; lower panel: wet condition).
Figure 13:
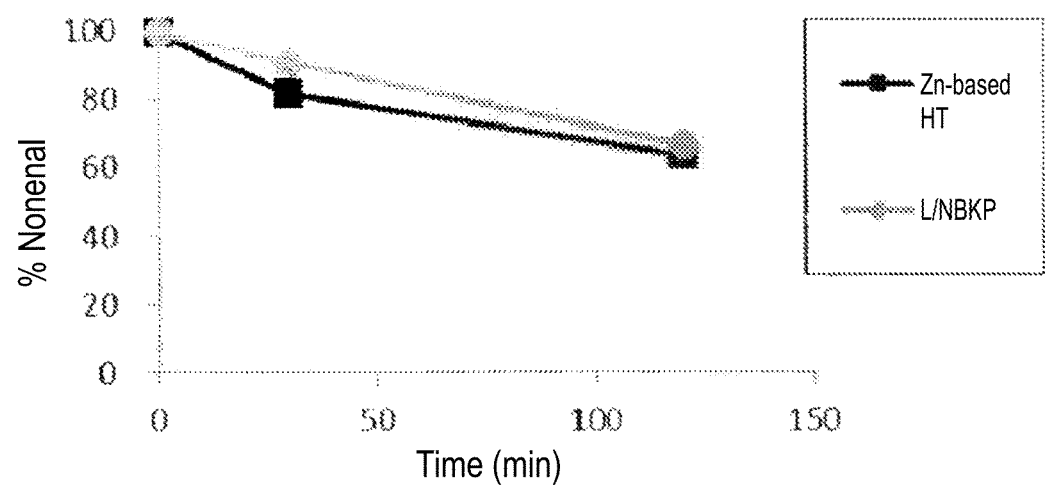

Further, the complexes obtained were observed by electron microscopy (SEM) to confirm that particles have been complexed onto the surfaces of the pulp fibers (FIG. 4). FIG. 4-1 shows electron micrographs of the mat prepared solely from the kraft pulp used for the preparation of Sample 1, demonstrating that no particles were found on the surface of the fiber. FIG. 4-2 shows electron micrographs of the mat prepared from the complex of Sample 1, demonstrating that many Mg-based HT microparticles deposited on the surface of the fiber in this complex. The coverage of the pulp fiber by the microparticles in the complex of Sample 1 (FIG. 4-2) was about 95% (wherein the microparticles had a primary particle size of about 40 to 60 nm and an average primary particle size of about 50 nm), in contrast to the complex of Sample 2 (FIG. 4-3) in which the coverage of the pulp fiber by the microparticles was about 75%. FIG. 4-4 shows electron micrographs of the mat prepared from the complex of Sample 3, demonstrating that many Zn-based HT microparticles deposited on the surface of the fiber (wherein the coverage of the pulp fiber by the microparticles was 50 to 80%, and the microparticles had a primary particle size of 100 to 900 nm and an average primary particle size of about 400 nm). FIG. 4-5 shows electron micrographs of the mat prepared from a mixture of Sample 0 and the kraft pulp. Particles were found on the surface of the fiber, but the coverage of the pulp fiber by the microparticles was 40 to 60%, which was lower than the value in the complex of Sample 1.

Furthermore, the ash content of the complex of Sample 1 (a complex of an Mg-based HT and a fiber) was determined to be 49.5% by weight, which approximately coincided with the theoretical value (50% by weight) calculated from the input ratio of the starting materials (the pulp and calcium hydroxide). The ash content of the complex of Sample 3 (a complex of a Zn-based HT and a fiber) was 49.8% by weight, which approximately coincided with the theoretical value (50% by weight) calculated from the input ratio of the starting materials (the pulp and calcium hydroxide). The ash content of each complex was calculated from the ratio between the weight of the residue remaining after the complex was heated at 525° C. for about 2 hours and the initial solids content (JIS P 8251: 2003). It should be noted that the ash content was calculated taking into account the weight loss from the actually measured weight after the ashing process because the weight decreases by decarbonation of hydrotalcite or elimination of interlayer water during the ashing process at 525° C. (Mg-based HT: about 40%, Zn-based HT: about 30%). Further, the proportion of Mg or Zn was calculated on the basis of the composition of each hydrotalcite.

(Sheets 1 and 2)

According to JIS P 8222, sheets were prepared from the complexes prepared in Experiment 1 (Samples 1 and 2). Specifically, an aqueous slurry (about 0.5%) of each complex was stirred with 100 ppm of a cationic retention aid (ND300 from HYMO CORPORATION) and 100 ppm of an anionic retention aid (FA230 from HYMO CORPORATION) at 500 rpm to prepare a suspension, and a sheet was prepared from the prepared suspension according to JIS P 8222.

(Sheet 3)

According to JIS P 8222, a sheet was prepared from the kraft pulp (CSF 390 ml) and hydrotalcite microparticles (Sample 0) described in Experiment 1. Specifically, an aqueous slurry (about 0.5%) of the LBKP/NBKP pulp mixture was combined with a hydrotalcite prepared in Experiment 1 and stirred with 100 ppm of a cationic retention aid (ND300 from HYMO CORPORATION) and 100 ppm of an anionic retention aid (FA230 from HYMO CORPORATION) at 500 rpm to prepare a suspension, and a sheet was prepared from the prepared suspension according to JIS P 8222.

(Sheets 4 and 5)

Complex sheets were prepared in the same manner as described for Sheets 1 and 2 except that neither cationic retention aid nor anionic retention aid was used.

(Sheet 6)

A complex sheet was prepared in the same manner as described for Sheet 3 except that neither cationic retention aid nor anionic retention aid was used. The retention was 62.1%.

(2) Evaluation of the Complex Sheets

Evaluations were made according to the following evaluation procedures.

Basis weight: JIS P 8124: 1998.
Thickness: JIS P 8118: 1998.

TABLE 1

Complex mats

| Number | HT complex | Ash % | Proportion of Mg or Zn in the ash % | Basis weight g/m$^2$ | Density g/m$^3$ |
|---|---|---|---|---|---|
| T-1 | Pulp alone (LBKP/NBKP = 8:2) | 0.5 | — | 111 | 0.46 |
| T-2 | Sample 1 (Mg-based HT complex obtained by adding an acid to an alkali) | 49.5 | 24.2 | 112 | 0.53 |
| T-3 | Sample 3 (Zn-based HT complex) | 49.8 | 46.1 | 111 | 0.51 |
| T-4 | Sample 4 (Ca carbonate complex) | 40.0 | — | 91 | 0.53 |
| T-5 | Sample 5 (Mg carbonate complex) | 43.0 | — | 107 | 0.42 |

Experiment 2: Preparation and Evaluation of Complex Sheets (1) Preparation of Complex Sheets
(Sheet 0)

According to JIS P 8222, a handsheet having a basis weight of about 60 g/m$^2$ was prepared from a kraft pulp. The pulp used was the same as described in Experiment 1, i.e., it comprises a bleached hardwood kraft pulp (LBKP from Nippon Paper Industries Co., Ltd.) and a bleached softwood kraft pulp (NBKP from Nippon Paper Industries Co., Ltd.) in a weight ratio of 8:2 and has been processed to a Canadian standard freeness of 390 ml using a single disc refiner (SDR).

Density: calculated from the measured thickness and basis weight.
Ash: JIS P 8251: 2003.
Brightness: JIS P 8212: 1998.
Opacity: JIS P 8149: 2000.
Specific scattering coefficient (S value): calculated by the equation defined in TAPPI T425 (ISO 9416).
Air resistance: JIS P8117: 2009.
Smoothness: JIS P 8155: 2010.
Bending load: calculated from the bending stiffness measured at a bending angle of 15° according to ISO-2493 using L&W Bending Tester (from Lorentzen & Wettre).
Breaking length: JIS P 8113: 2006.

X-ray diffraction: The sheet samples were analyzed in the same manner as described in Experiment 1 (FIG. 5).
Retention: calculated from the input amount used for preparing a sheet and the weight of the prepared sheet.

evaluate deodorant properties for sweat odor (ammonia, acetic acid, isovaleric acid), urine and feces odor (ammonia, acetic acid, hydrogen sulfide, methyl mercaptan, indole), old person smell (ammonia, acetic acid, isovaleric acid, non-

TABLE 2

| | | Sample | | | | | |
|---|---|---|---|---|---|---|---|
| | | 0 LBKP/NBKP | 1 HT complex A | 2 HT complex B | 3 HT-filled | 4 HT complex A | 5 HT complex B |
| (Retention aids) | | Yes | Yes | Yes | Yes | No | No |
| Basis weight | g/m² | 61.4 | 58.6 | 56.6 | 50.5 | 57.2 | 55.2 |
| Thickness 100 kPa | μm | 106 | 100 | 93 | 81 | 101 | 94 |
| Density 100 kPa | g/cm³ | 0.58 | 0.59 | 0.61 | 0.62 | 0.57 | 0.59 |
| Ash (theoretical value/0.6) | % | 0.4 | 32.1 | 26.7 | 30.4 | 27.4 | 23.5 |
| Brightness | % | 82.6 | 86.6 | 83.4 | 83.9 | 87.4 | 83.7 |
| Opacity | % | 73.9 | 69.4 | 66.5 | 59.0 | 70.0 | 66.4 |
| Specific scattering coefficient (S) | m²/kg | 33.5 | 31.3 | 28.0 | 23.6 | 33.1 | 28.7 |
| Air resistance | sec | 6 | 10 | 4 | 25 | 4 | 2 |
| Smoothness Wire side | sec | 5 | 6 | 5 | 5 | 6 | 5 |
| Smoothness Felt side | sec | 4 | 6 | 6 | 7 | 6 | 5 |
| Tensile strength | kN/m | 2.71 | 0.80 | 1.60 | 1.01 | 0.79 | 1.61 |
| Breaking length | km | 4.60 | 1.36 | 2.73 | 1.71 | 1.34 | 2.74 |
| Bending load | mN | 151 | 77 | 90 | 92 | 97 | 95 |
| Retention | % | 97.5 | 91.6 | 99.4 | 81.7 | 86.8 | 96.5 |

As shown in the table above, the hydrotalcite complexes synthesized by adding an acid to a suspension of a fiber and an alkali had higher brightness and opacity as well as higher fiber coverage and ash content as compared with the hydrotalcite complexes synthesized by adding an alkali to a suspension of a fiber and an acid. On the other hand, the hydrotalcite complexes synthesized by adding an alkali to a suspension of a fiber and an acid provided sheets having higher tensile strength as compared with the hydrotalcite complexes synthesized by adding an acid to a suspension of a fiber and an alkali.

Experiment 3: Evaluation of Deodorant Properties

The complex mats prepared in Experiment 1(3) (having a basis weight of about 100 g/m²) were used to evaluate the deodorant properties of the complexes. The complex mats subjected to the deodorant tests had a size of 100 cm² (10 cm×10 cm) except that the samples for assaying hydrogen sulfide, methyl mercaptan, and indole under wet condition described below had a size of 25 cm².

Deodorant tests were performed according to the procedure of the SEK mark textile product certification standard (JEC301, Japan Textile Evaluation Technology Council) to evaluate deodorant properties for sweat odor (ammonia, acetic acid, isovaleric acid), urine and feces odor (ammonia, acetic acid, hydrogen sulfide, methyl mercaptan, indole), old person smell (ammonia, acetic acid, isovaleric acid, nonenal), and garbage odor (ammonia, hydrogen sulfide, methyl mercaptan, trimethylamine). Ammonia, acetic acid, hydrogen sulfide, methyl mercaptan, pyridine, and trimethylamine were assayed by using a detector tube, while isovaleric acid, indole, and nonenal were assayed by gas chromatography.

(Condition 1: Dry Condition)

Each sample was conditioned at 20° C., 65% RH for 24 hours or more, and then evaluated for its deodorant properties for odor components (reduction in %). As used herein, the reduction (%) can be determined by the following equation from the initial concentration and the measured concentration of each odor component.

Reduction (%)=(1−measured concentration/initial concentration)×100

As shown in the table below and FIGS. 6 to 13, the mat T3 (Zn-based HT complex) demonstrated high deodorant effects for all odor components assayed among the samples subjected to the deodorant tests.

TABLE 3

Evaluation of deodorant effects under dry condition (reduction of odor components)

| | T1 Pulp alone | T2 Mg-based HT complex | T3 Zn-based HT complex | T4 Ca carbonate complex | T5 Mg carbonate complex | SEK standard (Reduction) |
|---|---|---|---|---|---|---|
| Ammonia | 67 | 51 | 97 | 36 | 66 | 80% |
| Acetic acid | 99 | 99 | 99 | 99 | 99 | 70% |
| Isovaleric acid | 92 | 98 | 99 | 99 | 99 | 95% |
| Hydrogen sulfide | 5 | 20 | 100 | — | — | 70% |
| Methyl mercaptan | 6 | 5 | 95 | — | — | 70% |
| Indole | 94 | 97 | 96 | — | — | 70% |
| Trimethylamine | 10 | — | 85 | — | — | 70% |
| Pyridine | 30 | — | 99 | — | — | 70% |
| Nonenal | 55 | — | 97 | — | — | 75% |

(Condition 2: Wet Condition)

Each sample was conditioned at 20° C., 65% RH for 24 hours or more and wetted by pipetting about 1 ml of water, and then evaluated for its deodorant properties for odor components. This test is intended to evaluate deodorant properties in a wet environment of a disposable diaper or the like.

As shown in the table below and FIGS. 6 to 13, higher deodorant effects were obtained for ammonia among the 5 odor components included in sweat odor under wet condition. This seems to result from the high water solubility of ammonia, which promotes odor adsorption.

Antibacterial activity={log(the number of viable cells after incubation with a control sample)−log(the number of viable cells immediately after inoculation onto the control sample)}−{log(the number of viable cells after incubation with a test sample)−log(the number of viable cells immediately after inoculation onto the test sample)}

TABLE 4

Evaluation of deodorant effects under wet condition (reduction of odor components)

|  | T1<br>Pulp alone | T2<br>Mg-based HT complex | T3<br>Zn-based HT complex | T4<br>Ca carbonate complex | T5<br>Mg carbonate complex |
|---|---|---|---|---|---|
| Ammonia | 84 | 94 | 99 | 80 | 72 |
| Acetic acid | 99 | 99 | 99 | 99 | 99 |
| Isovaleric acid | 99 | 98 | 99 | 99 | 99 |
| Hydrogen sulfide | 10 | 8 | 100 | — | — |
| Methyl mercaptan | 15 | 5 | 24 | — | — |
| Indole | 87 | 84 | 83 | — | — |
| Trimethylamine | 30 | — | 67 | — | — |
| Pyridine | 26 | — | 23 | — | — |
| Nonenal | 33 | — | 36 | — | — |

Experiment 4: Evaluation of Antibacterial Properties

According to JIS P 8222, a mat (having a basis weight of about 100 g/m$^2$ and an ash content of 46%) was prepared from a complex prepared in Experiment 1(2) (Sample 3). Specifically, an aqueous slurry (at a consistency of about 0.5%) of the complex containing 5000 ppm of a wet strengthening agent (brand name WS4024 from SEIKO PMC CORPORATION), 1200 ppm of an anionic retention aid (brand name FA230 from HYMO CORPORATION), and 1000 ppm of a cationic retention aid (brand name ND300 from HYMO CORPORATION) was filtered through a filter paper (Class 5B for quantitative analysis as defined by JIS P3801), and the resulting sample was dehydrated under a pressure of 1 MPa for 5 minutes, and then dried under tension at 50° C. for 2 hours to prepare a complex mat. The ash content of the complex was calculated from the ratio between the weight of the residue remaining after the complex was heated at 525° C. for about 2 hours and the initial solids content (JIS P 8251: 2003).

The complex mat prepared was used to evaluate its antibacterial properties. The complex mat subjected to the antibacterial tests had a weight of 0.4 g. A standard cotton cloth was used as a reference. The antibacterial tests were performed by the absorption method defined in JIS L 1902 (a quantitative assay in which the test bacterial suspension is inoculated directly onto specimens). Two test bacterial species *Staphylococcus aureus* (NBRC 12732) and *Escherichia coli* (NBRC 3301) were used to count the number of viable cells by the pour plate method after incubation for 18 hours. The assay protocol is shown below.
1. Place a 0.4-g specimen in a vial, add dropwise 0.2 ml of a test bacterial suspension (supplemented with 0.05% of a surfactant (Tween80)), and then cap the vial.
2. Incubate the vial at 37° C. for 18 hours.
3. Add 20 ml of a wash solution to wash away test bacterial cells from the specimen, and count the number of viable cells in the wash solution by the pour plate method or a luminescent assay.
4. Calculate the antibacterial activity by the equation below. If the antibacterial activity is 2.0 or more, it means that 99% or more of cells were killed.

As shown in the table below, the Zn-based HT complex subjected to the antibacterial tests demonstrated very high antibacterial properties against the assayed bacterial species.

TABLE 5

| Antibacterial activity | |
|---|---|
| Sample | Zn-based HT complex |
| *Staphylococcus aureus* | 6.0 |
| *Escherichia coil* | 6.2 |

It should be noted that the growth values determined by the antibacterial activity assay using a standard cotton cloth were 1.0 or more as shown in the table below, verifying that the assay was performed properly.

TABLE 6

| Growth value of test bacterial species | |
|---|---|
| Sample | Standard cotton cloth |
| *Staphylococcus aureus* | 2.9 |
| *Escherichia coil* | 3.1 |

Experiment 5: Evaluation of Antiviral Properties

A complex prepared in Experiment 1(2) (Sample 3) was treated with a thiosulfato copper complex solution to give Zn-based HT complexes (complexes of $Zn_6Al_2(OH)_{16}CO_3 \cdot 4H_2O$ and a pulp fiber) on which the thiosulfato copper complex solution has been deposited (Samples 6).

Specifically, copper chloride was dissolved, and the solution was mixed with a solution of sodium thiosulfate pentahydrate to prepare a thiosulfato copper complex solution. This thiosulfato copper complex solution was added to a slurry (at a consistency of 1.5%) of a complex prepared in Experiment 1(2) (Sample 3) at a copper concentration of 0.8 to 2.0% on a solids basis, and the mixture was stirred under conditions of 20° C. to 60° C. for 3 hours (Samples 6-1 to 6-3).

Subsequently, a mat (having a basis weight of about 100 g/m$^2$ and an ash content of 46%) was prepared according to JIS P 8222 from each of the complexes prepared (Samples 6-1 to 6-3). Specifically, an aqueous slurry (at a consistency of about 0.5%) of each complex was filtered through a filter paper (Class 5B for quantitative analysis as defined by JIS P3801), and the resulting sample was dehydrated under a pressure of 1 MPa for 5 minutes, and then dried under tension at 50° C. for 2 hours to prepare a complex mat.

The complex mat prepared was used to evaluate its antiviral properties. An antiviral activity assay was performed according to JIS L 1922: 2016 Textiles—Determination of antiviral activity of textile products. The complex mat subjected to the assay had a weight of 0.4 g, and a standard cotton cloth was used as a control sample. The test virus species used was Feline calicivirus (strain: F-9 ATCC VR-782). The assay protocol is shown below.

1. Place a 0.4-g specimen in a vial, add dropwise 0.2 ml of a test viral suspension, and then cap the vial.
2. Allow the vial to sit at 25° C. for 2 hours.
3. Add 20 ml of a wash solution to wash away viral cells from the specimen, and calculate the infectivity titer by a plaque assay.
4. Calculate the antiviral activity (Mv) by the equation below. JIS specifies that antiviral efficacy is achieved if $Mv \geq 2.0$ and it is sufficient if $Mv \geq 3.0$.

$$\text{Antiviral activity}(Mv) = \text{Log}(Vb) - \text{Log}(Vc)$$

Mv: Antiviral activity.

Log (Vb): The common logarithm of the infectivity titer in the control sample after exposure for 2 hours (the average of three specimens).

Log (Vc): The common logarithm of the infectivity titer in each antiviral test sample after exposure for 2 hours (the average of three specimens).

TABLE 7

| | | Antiviral activity | |
|---|---|---|---|
| Zn-based HT complex | Temperature ° C. | Cu loading % (on a solids basis) | Antiviral activity Log (Vb)-Log (Vc) |
| Sample 3 | | Untreated | 1.0 |
| Sample 6-1 | 60 | 0.8 | 3.4 |

TABLE 7-continued

| | | Antiviral activity | |
|---|---|---|---|
| Zn-based HT complex | Temperature ° C. | Cu loading % (on a solids basis) | Antiviral activity Log (Vb)-Log (Vc) |
| Sample 6-2 | 60 | 2.0 | 3.8 |
| Sample 6-3 | 20 | | 4.0 |

As shown in the table, the Zn-based HT complexes on which a thiosulfato copper complex solution has been adsorbed (Samples 6) demonstrated very high antiviral properties against the assayed virus species.

The invention claimed is:

1. A process for preparing a complex of a hydrotalcite and a cellulose fiber, wherein 60% or more of the surface of the cellulose fiber is covered with the hydrotalcite, and a proportion of hydrotalcite in the complex is 10% or more, comprising synthesizing the hydrotalcite in a solution containing the cellulose fiber, wherein the hydrotalcite is synthesized by:

(a) immersing the cellulose fiber in an alkaline solution, and then adding an acid solution to the immersed cellulose fiber; or
   (b) immersing the cellulose fiber in an acid solution, and then adding an alkaline solution to the immersed cellulose fiber,
   wherein the acid solution contains a divalent metal ion and a trivalent metal ion.

2. The process of claim 1, further comprising adding a solution containing an anionic material to the complex of a hydrotalcite and a cellulose fiber.

3. The process of claim 2, wherein the solution containing an anionic material is a copper- or silver-containing thiosulfato complex solution.

4. The process of claim 1, wherein the divalent metal ion in the acid solution is magnesium or zinc.

5. The process of claim 1, wherein the trivalent metal ion in the acid solution is aluminum.

6. The process of claim 1, wherein the complex of a hydrotalcite and a cellulose fiber contains 10% or more of magnesium or zinc based on the ash content.

7. The process of claim 1, wherein the proportion of hydrotalcite in the complex is 20% or more.

8. The process of claim 1, wherein the proportion of hydrotalcite in the complex is 40% or more.

* * * * *